(12) United States Patent
Hale et al.

(10) Patent No.: US 7,304,061 B2
(45) Date of Patent: Dec. 4, 2007

(54) HETEROCYCLIC INHIBITORS OF ERK2 AND USES THEREOF

(75) Inventors: Michael Robin Hale, Bedford, MA (US); Francois Maltais, Tewksbury, MA (US); Qing Tang, Acton, MA (US); Judith Straub, Cambridge, MA (US); Alexander Aronov, Watertown, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 136 days.

(21) Appl. No.: 10/424,280

(22) Filed: Apr. 25, 2003

(65) Prior Publication Data

US 2004/0029857 A1 Feb. 12, 2004

Related U.S. Application Data

(60) Provisional application No. 60/376,259, filed on Apr. 26, 2002, provisional application No. 60/403,853, filed on Aug. 14, 2002.

(51) Int. Cl.
  C07D 403/04 (2006.01)
  A61K 31/506 (2006.01)
(52) U.S. Cl. ............... 514/235.8; 514/255.05; 514/256; 514/275; 544/122; 544/316; 544/331; 544/333
(58) Field of Classification Search ........ 544/122, 544/316, 331, 333; 514/235.8, 256, 255.05, 514/275
See application file for complete search history.

(56) References Cited

U.S. PATENT DOCUMENTS 6,743,791 B2 * 6/2004 Cao et al. .............. 514/235.8

FOREIGN PATENT DOCUMENTS

| WO | WO 01/56993 | 8/2001 |
| WO | WO 01/57022 | 8/2001 |
| WO | WO 02/064586 | 8/2002 |
| WO | WO 02/079193 | 10/2002 |

OTHER PUBLICATIONS

Tanaka et al., PubMed Abstract (Cell 108(3):317-29) Feb. 2002.*
Rogers et al., PubMed Abstract (J Cell Biol. 157(2):219-29) Epub Apr. 2002.*
Casanova et al., PubMed Abstract (Rev Neurol. 28(9):909-15), May 1999.*
Hardt et al., Glycogen Synthase Kinase-3beta—A novel regulator of cardiac hypertrophy and development, Circulation Research, 90:1055-63, 2002.*
Douglas, Jr., Introduction to Viral Diseases, Cecil Textbook of Medicine, 20th Edition, vol. 2, pp. 1739-1747, 1996.*
Damasio, Alzheimer's Disease and related dementias, Cecil Textbook of Medicine, 20th Edition, vol. 2, pp. 1992-1996, 1996.*
Simone, Oncology: Introduction, Cecil Textbook of Medicine, 20th Edition, vol. 1, pp. 1004-1010, 1996.*
Layzer, Degenerative Diseases of the Nervous System, Cecil Textbook of Medicine, 20th Edition, vol. 2, pp. 2050-2057, 1996.*
Haar et al., CAPLUS Abstract 137:370099 (2002).*
Chang et al. "Role of cAMP-dependent pathway in eosinophil apoptosis and survival," Cell. Immunology. 203(1):29-38 (2000).
Frey et al. "TGF-beta regulation of mitogen-activated protein kinases in human breast cancer cells," Cancer Letters 117(1):41-50 (1997).
Fukunaga et al. "Role of MAP kinase in neurons," Molecular Neurobiology 16(1):79-95, (1998).
Hoshino et al., "Constitutive activation of the 41-/43-kDa mitogen-activated protein kinase signaling pathway in human tumors," Oncogene 18:813-22 (1999).
Hu et al. "Protein kinase and protein phosphatase expression in amyotrophic lateral sclerosis spinal cord," J. Neurochemistry. 85(2):432-42 (2003).
Illenberger et al. "The endogenous and cell cycle-dependent phosphorylation of tau protein in living cells: Implications for Alzheimer's disease," Molecular Biology of The Cell 9(6):1495-512 (1998).

(Continued)

*Primary Examiner*—Deepak Rao
(74) *Attorney, Agent, or Firm*—Daniel A. Pearson

(57) ABSTRACT

Described herein are compounds that are useful as protein kinase inhibitors having the formula:

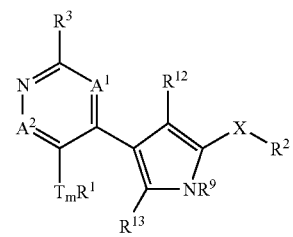

wherein $A^1$, $A^2$, $T_mR^1$, X, $R^2$, $R^3$, $R^9$, $R^{12}$, and $R^{13}$ are as described in the specification. The compounds are especially useful as inhibitors of ERK2, Aurora2, GSK3, CDK2, AKT3, and ROCK protein kinases and for treating diseases in mammals that are alleviated by a protein kinase inhibitor, particularly diseases such as cancer, neurodegenerative disorders, inflammatory disorders, restenosis, diabetes, and cardiovascular disease.

22 Claims, No Drawings

OTHER PUBLICATIONS

Kodama et al. "Significance of ERK cascade compared with JAK/STAT and PI3-K pathway in gp130-mediated cardiac hypertrophy," Am. J. Physiol. Heart Circ. Physiol. 279(4):H1635-44 (2000).

Kortylewski et al "Mitogen-activated protein kinases control p27/Kip1 expression and growth of human melanoma cells," Biochemical Journal 357(Pt 1):297-303 (2001).

Lee et al. "ICAM-1-induced expression of proinflammatory cytokines in astrocytes: Involvement of extracellular signal-regulated kinase and p38 mitogen-activated protein kinase pathways," The Journal of Immunology 165(8):4658-66 (2000).

Moses et al. "Injury-induced osteopontin gene expression in rat arterial smooth muscle cells is dependent on mitogen-activated protein kinases ERK1/ERK2," *Arch. Biochem. Biophys.* 396(1):133-7 (2001).

Namura et al. "Intravenous administration of MEK inhibitor U0126 affords brain protection against forebrain ischemia and focal cerebral ischemia," Proc. Natl. Acad. Sci. U S A 98(20):11569-74 (2001).

Pintucci et al. "Lack of ERK activation and cell migration in FGF-2-deficient endothelial cells," *FASEB J.* 16(6):598-600 (2002).

Putz et al. "Epidermal growth factor (EGF) receptor blockade inhibits the action of EGF, insulin-like growth factor I, and a protein kinase A activator on the mitogen-activated protein kinase pathway in prostate cancer cell lines," Cancer Research 59(1):227-33 (1999).

Raghunandan et al. "Hyperphosphorylation of the cytoskeletal protein Tau by the MAP-kinase PK40erk2: Regulation by prior phosphorylation with cAMP-dependent protein kinase A," Biochemical and Biophysical Research Communications 215(3):1056-66 (1995).

Slevin et al. "Activation of MAP kinase (ERK-1/ERK-2), tyrosine kinase and VEGF in the human brain following acute ischaemic stroke," NeuroReport 11(12):2759-64 (2000).

Tack et al. "Autocrine activation of the IGF-1 signaling pathway in mesangial cells isolated from diabetic NOD mice," Diabetes 51(1):182-8 (2002).

Takeishi et al. "Activation of mitogen-activated protein kinases and p90 ribosomal S6 kinase in failing human hearts with dilated cardiomyopathy," *Cardiovasc. Res.* 53(1):131-7 (2002).

* cited by examiner

HETEROCYCLIC INHIBITORS OF ERK2 AND USES THEREOF

CROSS REFERENCE TO RELATED APPLICATIONS

This application claims priority to U.S. Provisional Patent Application 60/376,259, filed Apr. 26, 2002 and U.S. Provisional Patent Application No. 60/403,853, filed Aug. 14, 2002, the contents of which are incorporated herein by reference.

FIELD OF THE INVENTION

The present invention is in the field of medicinal chemistry and relates to heterocyclic-pyrrole compounds that are protein kinase inhibitors, especially inhibitors of ERK, compositions comprising such compounds and methods of use. The compounds are useful for treating or alleviating cancer and other diseases that are alleviated by protein kinase inhibitors.

BACKGROUND OF THE INVENTION

Mammalian mitogen-activated protein (MAP) kinases are serine/threonine kinases that mediate intracellular signal transduction pathways (Cobb and Goldsmith, *J Biol. Chem.*, 270, 14843 (1995); Davis, *Mol. Reprod. Dev.*, 42, 459 (1995)). Members of the MAP kinase family share sequence similarity and conserved structural domains, and include the ERK2 (extracellular signal regulated kinase), JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., *Cell*, 76, 1025 (1994); Han et al., *Science*, 265, 808 (1994); Raingeaud et al., *J Biol. Chem.*, 270, 7420 (1995); Shapiro and Dinarello, *Proc. Natl. Acad. Sci. USA*, 92, 12230 (1995)). In contrast, ERKs are activated by mitogens and growth factors (Bokemeyer et al., *Kidney Int.*, 49, 1187 (1996)).

ERK2 is a widely distributed protein kinase that achieves maximum activity when both Thr183 and Tyr185 are phosphorylated by the upstream MAP kinase kinase, MEK1 (Anderson et al., *Nature*, 343, 651 (1990); Crews et al., *Science*, 258, 478 (1992)). Upon activation, ERK2 phosphorylates many regulatory proteins, including the protein kinases Rsk90 (Bjorbaek et al., *J. Biol. Chem.*, 270, 18848 (1995)) and MAPKAP2 (Rouse et al., *Cell*, 78, 1027 (1994)), and transcription factors such as ATF2 (Raingeaud et al., *Mol. Cell Biol.*, 16, 1247 (1996)), Elk-1 (Raingeaud et al. 1996), c-Fos (Chen et al., *Proc. Natl. Acad. Sci. USA*, 90, 10952 (1993)), and c-Myc (Oliver et al., *Proc. Soc. Exp. Biol. Med.*, 210, 162 (1995)). ERK2 is also a downstream target of the Ras/Raf dependent pathways (Moodie et al., *Science*, 260, 1658 (1993)) and relays the signals from these potentially oncogenic proteins. ERK2 has been shown to play a role in the negative growth control of breast cancer cells (Frey and Mulder, *Cancer Res.*, 57, 628 (1997)) and hyperexpression of ERK2 in human breast cancer has been reported (Sivaraman et al., *J. Clin. Invest.*, 99, 1478 (1997)). Activated ERK2 is also implicated in the proliferation of endothelin-stimulated airway smooth muscle cells, associating this kinase with asthma (Whelchel et al., *Am. J. Respir. Cell Mol. Biol.*, 16, 589 (1997)).

Aurora-2 is a serine/threonine protein kinase that is implicated in human cancer, such as colon, breast and other solid tumors. This kinase is involved in protein phosphorylation events that regulate the cell cycle. Specifically, Aurora-2 plays a role in controlling the accurate segregation of chromosomes during mitosis. Misregulation of the cell cycle can lead to cellular proliferation and other abnormalities. In human colon cancer tissue, the aurora-2 protein is overexpressed. See Bischoff et al., *EMBO J.*, 17, 3052-3065 (1998); Schumacher et al., *J. Cell Biol.*, 143, 1635-1646 (1998); Kimura et al., *J. Biol. Chem.*, 272, 13766-13771 (1997).

Glycogen synthase kinase-3 (GSK-3) is a serine/threonine protein kinase comprised of α and β isoforms that are each encoded by distinct genes (Coghlan et al., *Chemistry & Biology*, 7, 793-803 (2000); Kim and Kimmel, *Curr. Opinion Genetics Dev.*, 10, 508-514 (2000)). GSK-3 has been implicated in various diseases including diabetes, Alzheimer's disease, CNS disorders such as manic depressive disorder and neurodegenerative diseases, and cardiomyocete hypertrophy (WO 99/65897; WO 00/38675; and Haq et al., *J. Cell Biol.*, 151, 117 (2000)). These diseases are caused by, or result in, the abnormal operation of certain cell signaling pathways in which GSK-3 plays a role. GSK-3 phosphorylates and modulates the activity of a number of regulatory proteins. These proteins include glycogen synthase which is the rate limiting enzyme necessary for glycogen synthesis, the microtubule associated protein Tau, the gene transcription factor β-catenin, the translation initiation factor eIF2B, as well as ATP citrate lyase, axin, heat shock factor-1, c-Jun, c-Myc, c-Myb, CREB, and CEPBA. These diverse protein targets implicate GSK-3 in many aspects of cellular metabolism, proliferation, differentiation and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake (Klein et al., *PNAS*, 93, 8455-9 (1996); Cross et al., *Biochem. J*, 303, 21-26 (1994); Cohen, *Biochem. Soc. Trans.*, 21, 555-567 (1993); and Massillon et al., *Biochem J.*, 299, 123-128 (1994)). However, in a diabetic patient where the insulin response is impaired, glycogen synthesis and glucose uptake fail to increase despite the presence of relatively high blood levels of insulin. This leads to abnormally high blood levels of glucose with acute and long term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed (WO 00/38675). Therapeutic inhibitors of GSK-3 therefore are considered to be useful for treating diabetic patients suffering from an impaired response to insulin.

GSK-3 activity is associated with Alzheimer's disease. This disease is characterized by the well-known β-amyloid peptide and the formation of intracellular neurofibrillary tangles. The neurofibrillary tangles contain hyperphosphorylated Tau protein where Tau is phosphorylated on abnormal sites. GSK-3 phosphorylates these abnormal sites in cell and animal models. Furthermore, inhibition of GSK-3 prevents hyperphosphorylation of Tau in cells (Lovestone et al., *Current Biology*, 4, 1077-86 (1994); Brownlees et al., *Neuroreport*, 8, 3251-55 (1997)). Therefore, GSK-3 activity promotes generation of the neurofibrillary tangles and the progression of Alzheimer's disease.

Another substrate of GSK-3 is β-catenin which is degradated after phosphorylation by GSK-3. Reduced levels of β-catenin have been reported in schizophrenic patients and, have also been associated with other diseases related to increase in neuronal cell death (Zhong et al., *Nature*, 395, 698-702 (1998); Takashima et al., *PNAS*, 90, 7789-93 (1993); Pei et al., *J. Neuropathol. Exp*, 56, 70-78 (1997)).

AKT (also known as PKB or Rac-PK beta), a serine/threonine protein kinase, has been shown to be overexpressed in several types of cancer and is a mediator of normal cell functions (Khwaja, A., *Nature*, 401, 33-34 (1999); Yuan, Z. Q., et al., *Oncogene*, 19, 2324-2330 (2000); Namikawa, K., et al., *J Neurosci.*, 20, 2875-2886 (2000)). AKT comprises an N-terminal pleckstrin homology (PH) domain, a kinase domain and a C-terminal "tail" region. Three isoforms of human AKT kinase (AKT-1, -2 and -3) have been reported so far (Cheng, J. Q., *Proc. Natl. Acad. Sci. USA*, 89, 9267-9271 (1992); Brodbeck, D. et al., *J. Biol. Chem.*, 274, 9133-9136 (1999). The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) (Kulik et al., *Mol. Cell. Biol.*, 17, 1595-1606 (1997); Hemmings, B. A., *Science*, 275, 628-630 (1997). Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.*, 273, 7201-7204 (1998)) induction of differentiation and/or proliferation, protein synthesisans stress responses (Alessi, D. R. et al., *Curr. Opin. Genet. Dev.*, 8, 55-62 (1998)).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.*, 89, 9267-9271 (1992)). It has also been found to be overexpressed in 12% of pancreatic cancers (Cheng, J. Q. et al., *Proc. Natl. Acad. Sci. U.S.A.*, 93, 3636-3641 (1996)). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer*, 64, 280-285 (1995)). Cyclin-dependent kinases (CDKs) are serine/threonine protein kinases consisting of a β-sheet rich amino-terminal lobe and a larger carboxy-terminal lobe that is largely α-helical. The CDKs display the 11 subdomains shared by all protein kinases and range in molecular mass from 33 to 44 kD. This family of kinases, which includes CDK1, CKD2, CDK4, and CDK6, requires phosphorylation at the residue corresponding to CDK2 Thr160 in order to be fully active (Meijer, L., *Drug Resistance Updates*, 3, 83-88 (2000)).

Each CDK complex is formed from a regulatory cyclin subunit (e.g., cyclin A, B1, B2, D1, D2, D3, and E) and a catalytic kinase subunit (e.g., CDK1, CDK2, CDK4, CDK5, and CDK6). Each different kinase/cyclin pair functions to regulate the different and specific phases of the cell cycle known as the G1, S, G2, and M phases (Nigg, E., *Nature Reviews*, 2, 21-32 (2001); Flatt, P., Pietenpol, J., *Drug Metabolism Reviews*, 32, 283-305 (2000)).

The CDKs have been implicated in cell proliferation disorders, particularly in cancer. Cell proliferation is a result of the direct or indirect deregulation of the cell division cycle and the CDKs play a critical role in the regulation of the various phases of this cycle. For example, the overexpression of cyclin D1 is commonly associated with numerous human cancers including breast, colon, hepatocellular carcinomas and gliomas (Flatt, P., Pietenpol, J., *Drug Metabolism Reviews*, 32, 283-305 (2000)). The CDK2/cyclin E complex plays a key role in the progression from the early $G_1$ to S phases of the cell cycle and the overexpression of cyclin E has been associated with various solid tumors. Therefore, inhibitors of cyclins D1, E, or their associated CDKs are useful targets for cancer therapy (Kaubisch, A., Schwartz, G., *The Cancer Journal*, 6, 192-212 (2000)).

CDKs, especially CDK2, also play a role in apoptosis and T-cell development. CDK2 has been identified as a key regulator of thymocyte apoptosis (Williams, O. et al., *European Journal of Immunology*, 709-713 (2000)). Stimulation of CDK2 kinase activity is associated with the progression of apoptosis in thymocytes, in response to specific stimuli. Inhibition of CDK2 kinase activity blocks this apoptosis resulting in the protection of thymocytes.

In addition to regulating the cell cycle and apoptosis, the CDKs are directly involved in the process of transcription. Numerous viruses require CDKs for their replication process. Examples where CDK inhibitors restrain viral replication include human cytomegalovirus, herpes virus, and varicella-zoster virus (Meijer, L., *Drug Resistance Updates*, 3, 83-88 (2000)).

Inhibition of CDK is also useful for the treatment of neurodegenerative disorders such as Alzheimer's disease. The appearance of Paired Helical Filaments (PHF), associated with Alzheimer's disease, is caused by the hyperphosphorylation of Tau protein by CDK5/p25 (Meijer, L., *Drug Resistance Updates*, 3, 83-88 (2000)).

Another kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.*, 15, 1885-1893 (1996)) and ROKα/Rho-kinase/ROCK-II (Leung et al., *J. Biol. Chem.*, 270, 29051-29054 (1995); Matsui et al., *EMBO J.*, 15, 2208-2216 (1996); Nakagawa et al., *FEBS Lett.*, 392, 189-193 (1996)), protein kinase PKN (Amano et al., *Science*, 271, 648-650 (1996); Watanabe et al., *Science*, 271, 645-648 (1996)), and citron and citron kinase (Madaule et al. *Nature*, 394, 491-494 (1998); Madaule et al., *FEBS Lett.*, 377, 243-248 (1995)). The ROCK family of kinases have been shown to be involved in a variety of functions including Rho-induced formation of actin stress fibers and focal adhesions (Leung et al., *Mol. Cell Biol.*, 16, 5313-5327 (1996); Amano et al., *Science*, 275, 1308-1311 (1997); Ishizaki et al., *FEBS Lett.*, 404, 118-124 (1997)) and in downregulation of myosin phosphatase (Kimura et al., *Science*, 273, 245-248 (1996)), platelet activation (Klages et al., *J. Cell. Biol.*, 144, 745-754 (1999)), aortic smooth muscle contraction by various stimuli (Fu et al., *FEBS Lett.*, 440, 183-187 (1998)), thrombin-induced responses of aortic smooth muscle cells (Seasholtz et al., *Cir. Res.*, 84, 1186-1193 (1999)), hypertrophy of cardiomyocytes (Kuwahara et al., *FEBS Lett.,* 452, 314-318 (1999)), bronchial smooth muscle contraction (Yoshii et al., *Am. J. Respir. Cell Mol. Biol.,* 20, 1190-1200 (1999)), smooth muscle contraction and cytoskeletal reorganization of non-muscle cells (Fukata et al., *Trends in Pharm. Sci,* 22, 32-39 (2001)), activation of volume-regulated anion channels (Nilius et al., *J. Physiol.,* 516, 67-74 (1999)), neurite retraction (Hirose et al., *J. Cell. Biol.,* 141, 1625-1636 (1998)), neutrophil chemotaxis (Niggli, *FEBS Lett.,* 445, 69-72 (1999)), wound healing (Nobes and Hall, *J. Cell. Biol.,* 144, 1235-1244 (1999)), tumor invasion (Itoh et al., *Nat. Med.,* 5, 221-225 (1999)) and cell transformation (Sahai et al., *Curr. Biol.,* 9, 136-145 (1999)). Accordingly, the development of inhibitors of ROCK kinase would be useful as therapeutic agents for the treatment of disorders mediated by the ROCK kinase pathway.

There is a high unmet medical need to develop new therapeutic treatments that are useful in treating or preventing the various conditions associated with ERK2, GSK3, Aurora2, CDK2, AKT3, and ROCK activation. For many of these conditions the currently available treatment options are inadequate.

Accordingly, there is great interest in new and effective inhibitors of protein kinase, including ERK2, GSK3, Aurora2, CDK2, AKT3, and ROCK inhibitors, that are useful in treating or preventing various conditions associated with protein kinase activation.

SUMMARY OF THE INVENTION

The present invention provides compounds, and pharmaceutically acceptable derivatives thereof, that are useful as protein kinase inhibitors, particularly ERK2, GSK3, Aurora2, CDK2, AKT3, and ROCK. These compounds can be used alone or in combination with other therapeutic or prophylactic agents, such as chemotherapeutic or other anti-proliferative agents, immunomodulators or other anti-inflammatory agents, for the treatment or prophylaxis of diseases mediated by protein kinases, including ERK2, GSK3, Aurora2, CDK2, AKT3, and ROCK. According to a preferred embodiment, the compounds of this invention are capable of binding to the active site of ERK2, GSK3, Aurora2, CDK2, AKT3, and ROCK and inhibiting the activity of that enzyme.

It is a principal object of this invention to provide novel classes of compounds that are protein kinase inhibitors represented by formula I:

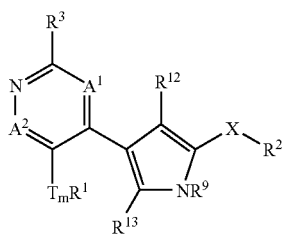

I wherein $A^1$, $A^2$, $T_mR^1$, X, $R^2$, $R^3$, $R^9$, $R^{12}$ and $R^{13}$ are as described herein.

It is a further objective of this invention to provide pharmaceutical compositions comprising the protein kinase inhibitors of this invention. In a preferred embodiment, the protein kinase inhibitors inhibit ERK2, GSK3, Aurora2, CDK2, AKT3, and ROCK. These compositions may be utilized in methods for treating or preventing a variety of protein kinase-mediated disorders, such as cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. Each of the above-described methods is also part of the present invention.

It is a further objective of this invention to provide methods for making the compounds and compositions of this invention.

DESCRIPTION OF THE INVENTION

According to one embodiment, the present invention relates to a compound of formula I:

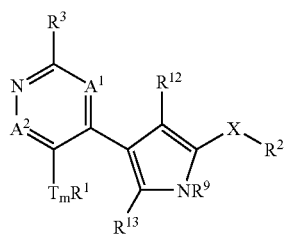

I or a pharmaceutically acceptable salt or derivative thereof, wherein:

$A^1$ is selected from N or $CR^{10}$;

$A^2$ is selected from N or $CR^{11}$;

T is selected from $-C(R^7)_2-$, $-C(O)-$, $-C(O)C(O)-$, $-C(O)NR^7-$, $-C(O)NR^7NR^7-$, $-CO_2-$, $-OC(O)-$, $-NR^7CO_2-$, $-O-$, $-NR^7C(O)NR^7-$, $-OC(O)NR^7-$, $-NR^7NR^7-$, $-NR^7C(O)-$, $-S-$, $-SO-$, $-SO_2-$, $-NR^7-$, $-SO_2NR^7-$, $-NR^7O_2-$, or $-NR^7O_2NR^7-$;

m is selected from zero or one;

$R^1$ is selected from: (a) hydrogen, CN, halogen, R, $N(R^7)_2$, OR, or OH, wherein m is zero; or (b) hydrogen or R, wherein m is one;

X is selected from $-C(O)-$, $-C(O)NR^7-$, $-NR^7C(O)-$, $-NR^7SO_2-$, $-SO_2NR^7-$, $-S(O)-$, or $-SO_2-$;

$R^2$ is selected from $-(CH_2)_yR^5$, $-(CH_2)_yCH(R^5)_2$, $-(CH_2)_yCH(R^8)(R^5)$, $-(CH_2)_yCH(R^8)CH(R^5)_2$, $-N(R^4)_2$, $-NR^4(CH_2)_yN(R^4)_2$, $-ON(R^7)_2$, or $-NR^7OR^6$;

y is 0-6;

$R^3$ is selected from $-R$, $-OR^6$, $-SR^6$, $-S(O)R^6$, $-SO_2R^6$, $-ON(R^7)_2$, $-N(R)_2$, $-NRN(R^7)_2$, or $-NROR^6$;

$R^6$ is selected from hydrogen or $-R$;

each R is independently selected from an optionally substituted group selected from $C_{1-6}$ aliphatic; 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen;

each $R^4$ is independently selected from —R, —$R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from —R, —OR, —$CO_2R$, —$(CH_2)_yN(R^7)_2$, —$N(R^7)_2$, —$OR^7$, —$SR^7$, —$NR^7C(O)R^7$, —$NR^7CON(R^7)_2$, —$C(O)N(R^7)_2$, —$SO_2R^7$, —$NR^7SO_2R^7$, —$C(O)R^7$, —CN, or —$SO_2N(R^7)_2$;

each $R^7$ is independently selected from hydrogen or an optionally substituted $C_{1-6}$ aliphatic group, or two $R^7$ groups bound to the same nitrogen are taken together with the nitrogen to form a 3-7 membered heterocyclic ring having 0-2 heteroatoms in addition to the nitrogen, independently selected from nitrogen, oxygen, or sulfur;

$R^8$ is selected from —R, —$(CH_2)_wOR^7$, —$(CH_2)_wN(R^4)_2$, or —$(CH_2)_wSR^7$;

each w is independently selected from 0-4;

$R^9$ is selected from hydrogen, an optionally substituted $C_{1-6}$ aliphatic group, $C(O)R^7$, $C(O)OR^7$, or $SO_2R^7$;

$R^{10}$ is selected from $R^7$, halogen, CN, $NO_2$, $OR^7$, $SR^7$, $N(R^7)_2$, $C(O)R^7$, or $CO_2R^7$; or $R^{10}$ and $R^3$ are taken together to form an optionally substituted 5-7 membered saturated, partially saturated, or aromatic ring having 0-2 heteroatoms independently selected from nitrogen, oxygen, and sulfur;

$R^{11}$ is selected from $R^7$, halogen, CN, $NO_2$, $OR^7$, $SR^7$, $N(R^7)_2$, $C(O)R^7$, or $CO_2R^7$;

$R^{12}$ is selected from $R^6$, $R^7$, CN, $NO_2$, halogen, $N(R^7)_2$, $SR^7$, and $OR^7$; and $R^{13}$ is selected from $R^6$, $R^7$, CN, $NO_2$, halogen, $N(R^7)_2$, $SR^7$, and $OR^7$.

provided that only one of $R^{12}$ and $R^{13}$ is a 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen.

As used herein, the following definitions shall apply unless otherwise indicated. The phrase "optionally substituted" is used interchangeably with the phrase "substituted or unsubstituted." Unless otherwise indicated, an optionally substituted group may have a substituent at each substitutable position of the group, and each substitution is independent of the other.

The term "aliphatic" or "aliphatic group" as used herein means a straight-chain or branched $C_1$-$C_{12}$ hydrocarbon chain that is completely saturated or that contains one or more units of unsaturation, or a monocyclic $C_3$-$C_8$ hydrocarbon or bicyclic $C_8$-$C_{12}$ hydrocarbon that is completely saturated or that contains one or more units of unsaturation, but which is not aromatic (also referred to herein as "carbocycle" or "cycloalkyl"), that has a single point of attachment to the rest of the molecule wherein any individual ring in said bicyclic ring system has 3-7 members. For example, suitable aliphatic groups include, but are not limited to, linear or branched or alkyl, alkenyl, alkynyl groups and hybrids thereof such as (cycloalkyl)alkyl, (cycloalkenyl)alkyl or (cycloalkyl)alkenyl.

The terms "alkyl", "alkoxy", "hydroxyalkyl", "alkoxyalkyl", and "alkoxycarbonyl", used alone or as part of a larger moiety includes both straight and branched chains containing one to twelve carbon atoms. The terms "alkenyl" and "alkynyl" used alone or as part of a larger moiety shall include both straight and branched chains containing two to twelve carbon atoms.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or $NR^+$ (as in N-substituted pyrrolidinyl).

The term "aryl" used alone or as part of a larger moiety as in "aralkyl", "aralkoxy", or "aryloxyalkyl", refers to monocyclic, bicyclic and tricyclic carbocyclic ring systems having a total of five to fourteen ring members, wherein at least one ring in the system is aromatic and wherein each ring in the system contains 3 to 8 ring members. The term "aryl" may be used interchangeably with the term "aryl ring".

The term "heterocycle", "heterocyclyl", or "heterocyclic" as used herein means monocyclic, bicyclic or tricyclic ring systems having five to fourteen ring members in which one or more ring members is a heteroatom, wherein each ring in the system contains 3 to 7 ring members and is non-aromatic.

The term "heteroaryl", used alone or as part of a larger moiety as in "heteroaralkyl" or "heteroarylalkoxy", refers to monocyclic, bicyclic and tricyclic ring systems having a total of five to fourteen ring members, and wherein: 1) at least one ring in the system is aromatic; 2) at least one ring in the system contains one or more heteroatoms; and 3) each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl, heteroarylalkoxy and the like) group may contain one or more substituents. Substituents on the unsaturated carbon atom of an aryl, heteroaryl, aralkyl, or heteroaralkyl group are selected from halogen; haloalkyl; —$CF_3$; —$R°$; —$OR°$; —$SR°$; 1,2-methylene-dioxy; 1,2-ethylenedioxy; dimethyleneoxy; protected OH (such as acyloxy); phenyl (Ph); Ph substituted with $R°$; —O(Ph); —O-(Ph) substituted with $R°$; —$CH_2$(Ph); —$CH_2$(Ph) substituted with $R°$; —$CH_2CH_2$(Ph); —$CH_2CH_2$(Ph) substituted with $R°$; —$NO_2$; —CN; —$N(R°)_2$; —$NR°C(O)R°$; —$NR°C(O)N(R°)_2$; —$NR°CO_2R°$; —$NR°NR°C(O)R°$; —$NR°NR°C(O)N(R°)_2$; —$NR°NR°CO_2R°$; —$C(O)C(O)R°$; —$C(O)CH_2C(O)R°$; —$CO_2R°$; —$C(O)R°$; —$C(O)N(R°)_2$; —$OC(O)N(R°)_2$; —$S(O)_2R°$; —$SO_2N(R°)_2$; —$S(O)R°$; —$NRSO_2N(R°)_2$; —$NRSO_2R°$; —$C(=S)N(R°)_2$; —$C(=NH)$—$N(R°)_2$; —$(CH_2)_yNHC(O)R°$; —$(CH_2)_yR°$; —$(CH_2)_yNHC(O)NHR°$; —$(CH_2)_yNHC(O)OR°$; —$(CH_2)_yNHS(O)R°$; —$(CH_2)_yNHSO_2R°$; or —$(CH_2)_yNHC(O)CH(V_z$—$R°)(R°)$, wherein each $R°$ is independently selected from hydrogen, optionally substituted $C_{1-6}$ aliphatic, an unsubstituted 5-6 membered heteroaryl or heterocyclic ring, phenyl (Ph), —O(Ph), or —$CH_2$(Ph)-$CH_2$(Ph), wherein y is 0-6; z is 0-1; and V is a linker group. When $R°$ is $C_{1-6}$ aliphatic, it is optionally substituted with one or more substituents selected from —$NH_2$, —$NH(C_{1-4}$ aliphatic), —$N(C_{1-4}$ aliphatic$)_2$, —$S(O)(C_{1-4}$ aliphatic), —$SO_2(C_{1-4}$ aliphatic), halogen, —$(C_{1-4}$ aliphatic), —OH, —O—$(C_{1-4}$ aliphatic), —$NO_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

An aliphatic group or a non-aromatic heterocyclic ring may contain one or more substituents. Substituents on the saturated carbon of an aliphatic group or of a non-aromatic heterocyclic ring are selected from those listed above for the unsaturated carbon of an aryl or heteroaryl group and the following: =O, =S, =NN(R*)$_2$, =N—, =NNHC(O)R*, =NNHCO$_2$(alkyl), =NNHSO$_2$(alkyl), or =NR*, where each R* is independently selected from hydrogen or an optionally substituted C$_{1-6}$ aliphatic. When R* is C$_{1-6}$ aliphatic, it is optionally substituted with one or more substituents selected from —NH$_2$, —NH(C$_{1-4}$ aliphatic), —N(C$_{1-4}$ aliphatic)$_2$, halogen, —OH, —O—(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

Substituents on the nitrogen of a non-aromatic heterocyclic ring are selected from —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, or —NR$^+$SO$_2$R$^+$; wherein each R$^+$ is independently selected from hydrogen, an optionally substituted C$_{1-6}$ aliphatic, optionally substituted phenyl (Ph), optionally substituted —O(Ph), optionally substituted —CH$_2$(Ph), optionally substituted —CH$_2$CH$_2$(Ph), or an unsubstituted 5-6 membered heteroaryl or heterocyclic ring. When R$^+$ is a C$_{1-6}$ aliphatic group or a phenyl ring, it is optionally substituted with one or more substituents selected from —NH$_2$, —NH(C$_{1-4}$ aliphatic), —N(C$_{14}$ aliphatic)$_2$, halogen, —(C$_{1-4}$ aliphatic), —OH, —O—(C$_{1-4}$ aliphatic), —NO$_2$, —CN, —CO$_2$H, —CO$_2$(C$_{1-4}$ aliphatic), —O(halo C$_{1-4}$ aliphatic), or -halo(C$_{1-4}$ aliphatic); wherein each C$_{1-4}$ aliphatic is unsubstituted.

The term "linker group" or "linker" means an organic moiety that connects two parts of a compound. Linkers are comprised of —O—, —S—, —NR*—, —C(R*)$_2$—, —C(O)—, or an alkylidene chain. The alkylidene chain is a saturated or unsaturated, straight or branched, C$_{1-6}$ carbon chain which is optionally substituted, and wherein up to two non-adjacent saturated carbons of the chain are optionally replaced by —C(O)—, —C(O)C(O)—, —C(O)NR*—, —C(O)NR*NR*—, —CO$_2$—, —OC(O)—, —NR*CO$_2$—, —O—, —NR*C(O)NR*—, —OC(O)NR*—, —NR*NR*—, —NR*C(O)—, —S—, —SO—, —SO$_2$—, —NR*—, —SO$_2$NR*—, or —NR*SO$_2$—; wherein R* is selected from hydrogen or C$_{1-4}$ aliphatic. Optional substituents on the alkylidene chain are as described above for an aliphatic group.

The compounds of this invention are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}$C- or $^{14}$C-enriched carbon are within the scope of this invention.

Compounds of this invention may exist in alternative tautomeric forms. Unless otherwise indicated, the representation of either tautomer is meant to include the other.

One embodiment of the present invention relates to compounds of formula I wherein the functional group R$^3$ is attached to the pyrimidine ring via a nitrogen linkage (II-A, II-B, and II-C), via a sulfur linkage (III-A, III-B, and III-C), via an oxygen linkage (IV-A and IV-B), or is R (V-A) as shown below:

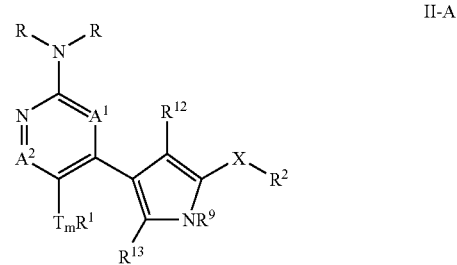

II-A

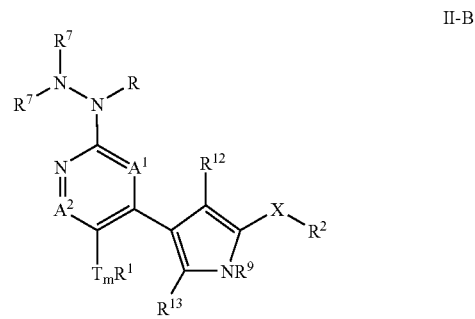

II-B

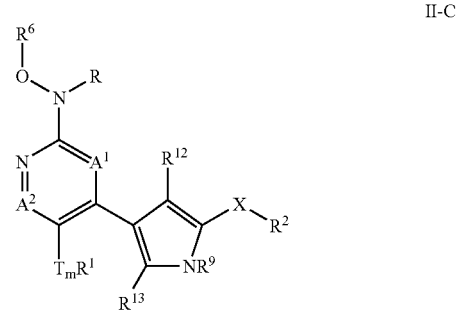

II-C

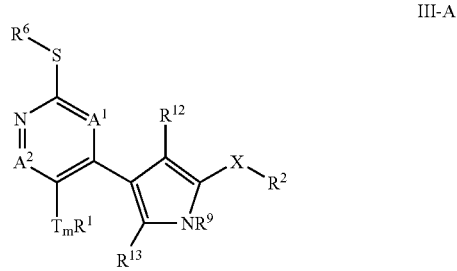

III-A

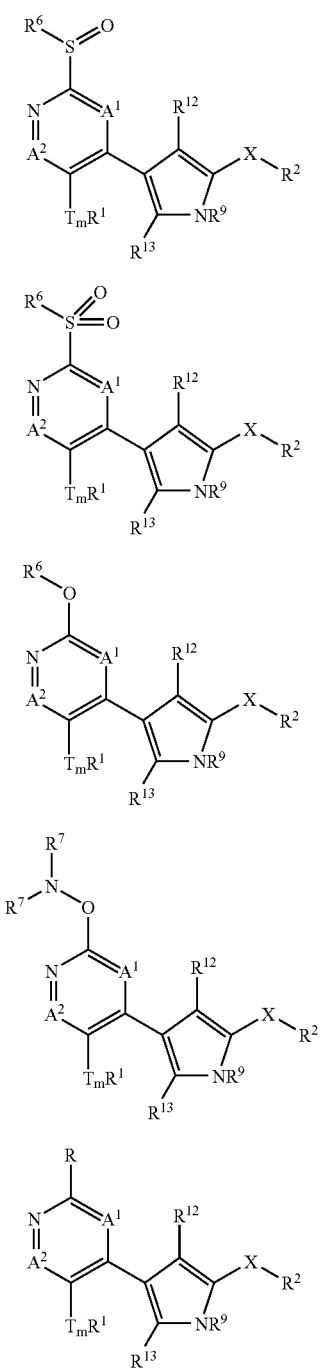

or a pharmaceutically acceptable salt or derivative thereof, wherein $A^1$, $A^2$, $T_mR^1$, X, $R^2$, R, $R^6$, $R^7$, $R^9$, $R^{12}$, and $R^{13}$ are as described above.

In one preferred embodiment, $A^1$ is N and $A^2$ is CH. In another preferred embodiment, $A^1$ and $A^2$ are both CH.

When $A^1$ is C—$R^{10}$, and the $R^3$ and C—$R^{10}$ groups of formula I, or of any of subformulae II-A, II-B, II-C, III-A, III-B, III-C, IV-A, IV-B, and V-A are taken together to form an optionally substituted ring, preferred rings formed thereby are 5-6 membered saturated, partially saturated, or aromatic rings having 0-2 heteroatoms independently selected from nitrogen, oxygen, or sulfur. More preferred rings formed by the $R^3$ and $R^{10}$ groups are 5-6 membered saturated, partially saturated, or aromatic rings having 0-2 nitrogen atoms. Examples of such rings formed by the $R^3$ and $R^{10}$ groups include optionally substituted pyrrolidino, pyrrolo, and imidazolo rings.

Preferred $T_mR^1$ groups of formula I, or of the subformulae II-A, II-B, II-C, III-A, III-B, III-C, IV-A, IV-B, and V-A are selected from hydrogen, $N(R^7)_2$, OH, 3-6 membered carbocyclyl, or an optionally substituted group selected from $C_{1-6}$ aliphatic or a 5-6 membered aryl or heteroaryl ring. When $R^1$ is an optionally substituted phenyl or aliphatic group, preferred substituents on the phenyl or aliphatic group are methyl, ethyl, halo, nitro, alkoxy, hydroxy and amino. Preferred $T_mR^1$ groups are methyl, ethyl, propyl, cyclopropyl, cyclohexyl, phenyl, $CH_2OCH_3$, $CH_2OH$, $NH_2$, $NHCH_3$, NHAc, $NHC(O)NHCH_3$, and $CH_2NHCH_3$. More preferred $T_mR^1$ groups of formula I are those listed in Table 1 below.

Preferred X is selected from —C(O)— or —C(O)$NR^7$—.
Preferred $R^3$ groups of formula I are selected from —N(optionally substituted $C_{1-6}$ aliphatic)$_2$; —SH; —S($C_{1-6}$ aliphatic); —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring. More preferred $R^3$ groups of formula I are those listed in Table 1 below.

When $R^2$ is $R^5$ (i.e., where $R^2$ is —$(CH_2)_yR^5$ and y is zero) preferred $R^5$ groups are pyrrolidin-1-yl, morpholin-4-yl, piperidin-1-yl, and piperazin-1-yl, 4-methyl[1,4]diazepan-1-yl, 4-phenyl-piperazine-1-yl, wherein each group is optionally substituted. When $R^2$ is —$(CH_2)_yR^5$, or —$(CH_2)_y$CH$(R^5)_2$ or —N$(R^4)_2$, and $R^4$ is —$(CH_2)_yR^5$ or —$(CH_2)_y$CH$(R^5)_2$, preferred $R^5$ groups are further selected from pyridin-3-yl, pyridin-4-yl, imidazolyl, furan-2-yl, 1,2,3,4-tetrahydroisoquinoline, tetrahydrofuran-2-yl, cyclohexyl, phenyl, benzyl, —$CH_2OH$, —$(CH_2)_2OH$, —$CH_2NH_2$, —$(CH_2)_2NH_2$, and isopropyl, wherein each group is optionally substituted. Preferred substituents on the $R^5$ group are —OH, pyridyl, piperidinyl, and optionally substituted phenyl. When $R^2$ is —$(CH_2)_y$CH$(R^8)(R^5)$ or —$(CH_2)_y$CH$(R^8)$CH$(R^5)_2$, preferred $R^8$ groups are —$(CH_2)_w$O$R^7$ or —$(CH_2)_w$ N$(R^4)_2$ such as OH, $NH_2$, $CH_2OH$, $CH_2NH_2$, and $CH_2CH_2NH_2$ and preferred $R^5$ are as described above. Preferred —$(CH_2)_y$CH$(R^8)$CH$(R^5)_2$ groups of formula I, or of any of the subformulae II-A, II-B, II-C, III-A, III-B, III-C, IV-A, IV-B, and V-A are —CH(OH)CH(OH)phenyl, —CH(Me)CH($NH_2$)phenyl, —CH($CH_2NH_2$)CH(Me)phenyl, and —CH(Me)CH(OH)phenyl, wherein phenyl is optionally substituted. Preferred —$(CH_2)_y$CH$(R^8)(R^5)$ groups of formula I, or of any of the subformulae II-A, II-B, II-C, II-A, III-B, III-C, IV-A, IV-B, and V-A are —CH(phenyl)$CH_2OH$ or —CH(phenyl)$CH_2NH_2$, wherein phenyl is optionally substituted. Other preferred —$R^2$ groups are those listed in Table I below.

Preferred $R^9$ groups of formula I, or of any of the subformulae II-A, II-B, II-C, III-A, III-B, III-C, IV-A, IV-B, and V-A are selected from hydrogen, optionally substituted $C_{1-4}$ aliphatic, C(O)$R^7$, and C(O)O$R^7$. Most preferred $R^9$ groups of formula I are selected from hydrogen, methyl, ethyl, C(O)Me, C(O)OCH$_2$phenyl, and CH$_2$phenyl. Most preferably, the $R^9$ group is hydrogen.

Preferred $R^{12}$ and $R^{13}$ groups of formula I, or of any of the subformulae II-A, II-B, II-C, III-A, III-B, III-C, IV-A, IV-B, and V-A are independently selected from hydrogen, methyl, or ethyl. Most preferably, each $R^{12}$ and $R^{13}$ group is hydrogen.

Preferred compounds of formula I, or of any of the subformulae II-A, II-B, II-C, III-A, III-B, III-C, IV-A, IV-B, and V-A are those having one, more preferably more than one, and most preferably all, of the features selected from the group consisting of:
- (a) X is selected from —C(O)— or —C(O)NR$^7$—;
- (b) R$^3$ is —N(optionally substituted C$_{1-6}$ aliphatic)$_2$; —SH; —S(C$_{1-6}$ aliphatic); —OH; —O(C$_{1-6}$ aliphatic); 3-6 membered carbocyclyl; or an optionally substituted group selected from C$_{1-6}$ aliphatic or a 5-6 membered aryl, heteroaryl, or heterocyclyl ring;
- (c) T$_m$R$^1$ is hydrogen, amino, OH, 3-6 membered carbocyclyl, or an optionally substituted group selected from C$_{1-6}$ aliphatic or a 5-6 membered aryl or heteroaryl ring;
- (d) R$^2$ is —NR$^4$(CH$_2$)$_y$N(R$^4$)$_2$—(CH$_2$)$_y$R$^5$, —(CH$_2$)$_y$CH(R$^5$)$_2$, —(CH$_2$)$_y$CH(R$^8$)(R$^5$), or —(CH$_2$)$_y$CH(R$^8$)CH(R$^5$)$_2$;
- (e) R$^4$ is R, R$^7$, or —(CH$_2$)$_y$CH(R$^5$)$_2$; and
- (f) R$^5$ is an optionally substituted group selected from C$_{1-6}$ aliphatic, phenyl, naphthyl, 5-6 membered heteroaryl, or 5-6 membered heterocyclyl.

More preferred compounds of formula I, or of any of the subformulae II-A, II-B, II-C, III-A, III-B, III-C, IV-A, IV-B, and V-A are those having one or more, more preferably more than one, or most preferably all, of the features selected from the group consisting of:
- (a) X is —C(O)—;
- (b) R$^3$ is selected from optionally substituted phenyl, methyl, ethyl, propyl, cyclopropyl, N(methyl)$_2$, N(ethyl)$_2$, N(CH$_2$CH$_2$OH)$_2$, pyridinyl, morpholinyl, piperidinyl, piperazinyl, S-methyl, OH, O-methyl, O-ethyl, or —CH$_2$-morpholin-4-yl;
- (c) T$_m$R$^1$ is selected from optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$;
- (d) R$^2$ is —(CH$_2$)$_y$R$^5$, —(CH$_2$)$_y$CH(R$^5$)$_2$, —(CH$_2$)$_y$CH(R$^8$)(R$^5$), or —(CH$_2$)$_y$CH(R$^8$)CH(R$^5$)$_2$, wherein R$^8$ is OH, NH$_2$, CH$_2$OH, CH$_2$NH$_2$, or CH$_2$CH$_2$NH$_2$; and
- (e) R$^5$ is —CH$_2$OH, —(CH$_2$)$_2$OH, isopropyl, or an optionally substituted group selected from pyrrolidinyl, morpholinyl, piperidinyl, piperazinyl, methyldiazepanyl, phenylpiperazineyl, pyridinyl, imidazolyl, furanyl, tetrahydroisoquinoline, tetrahydrofuranyl, cyclohexyl, phenyl, or benzyl.

A preferred embodiment of this invention relates to compounds of formula I':

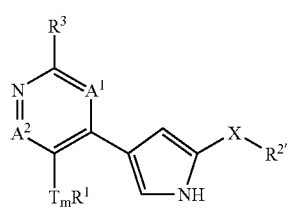

I' or a pharmaceutically acceptable salt or derivative thereof, wherein:
R$^{2'}$ is selected from —(CH$_2$)$_y$CH(R$^5$)$_2$, —(CH$_2$)$_y$CH(R$^8$)(R$^5$), or —(CH$_2$)$_y$CH(R$^8$)CH(R$^8$)$_2$;
and A$^1$, A$^2$, T, m, R$^1$, X, R$^3$, y, R$^5$, and R$^8$ are as described above.

The present invention relates to compounds of formula I' wherein the functional group R$^3$ is attached to the pyrimidine ring via a nitrogen linkage (II-A', II-B', and II-C'), via a sulfur linkage (III-A', III-B', III-C'), via an oxygen linkage (IV-A' and IV-B'), or is R (V-A') as shown below:

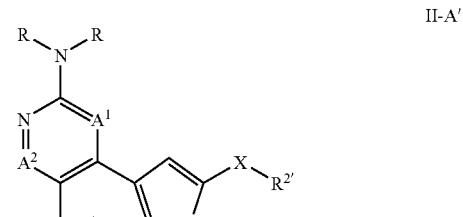

II-A'

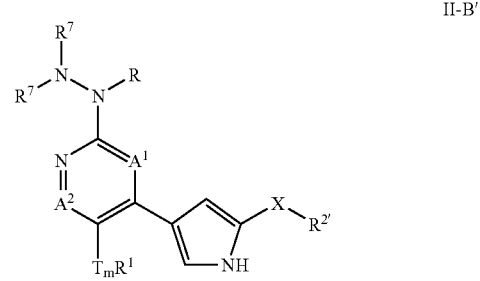

II-B'

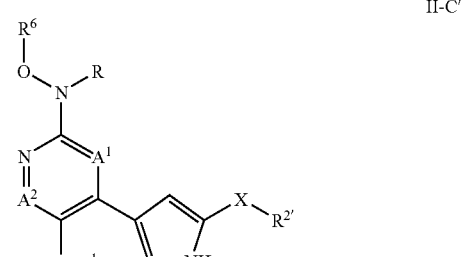

II-C'

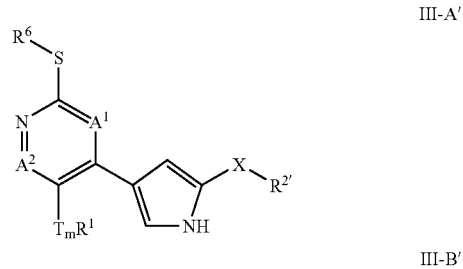

III-A'

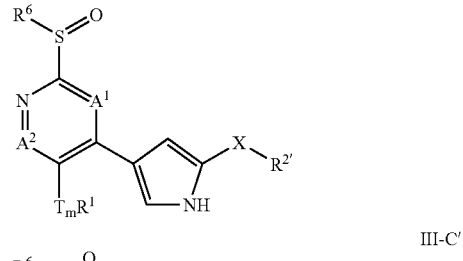

III-B'

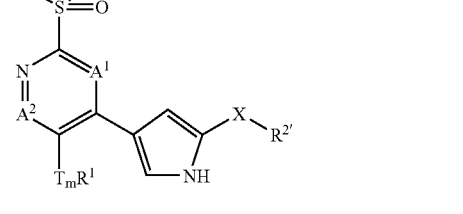

III-C'

-continued

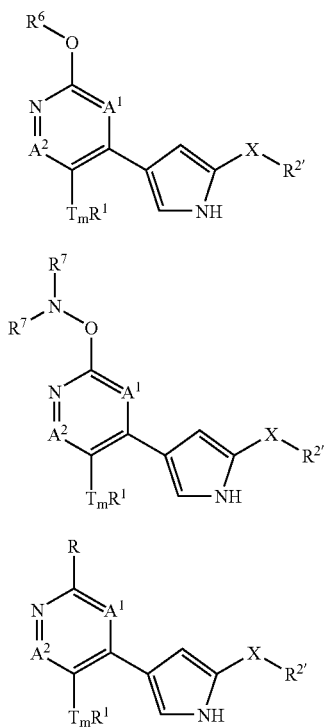

or a pharmaceutically acceptable salt or derivative thereof, wherein $A^1$, $A^2$, $T_mR^1$, X, $R^{2'}$, R, $R^6$ and $R^7$ are as described above.

Preferred $A^1$, $A^2$, $T_mR^1$, X, and $R^3$ groups of formula I', or of any of the subformulae II-A', II-B', II-C', III-A', III-B', III-C', IV-A', IV-B', and V-A' are as described above for formula I and subformulae II-A, II-B, II-C, III-A, III-B, III-C, IV-A, IV-B, and V-A.

Preferred compounds of formula I', or of any of the subformulae II-A', II-B', II-C', III-A', III-B', III-C', IV-A', IV-B', and V-A' are those having one or more, more preferably more than one, and most preferably all, of the features selected from the group consisting of:
 (a) X is selected from —C(O)— or —C(O)NR$^7$—;
 (b) $R^3$ is —N(optionally substituted $C_{1-6}$ aliphatic)$_2$; —SH; —S($C_{1-6}$ aliphatic); —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;
 (c) $T_mR^1$ is hydrogen, amino, OH, 3-6 membered carbocyclyl, or an optionally substituted group selected from $C_{1-6}$ aliphatic or a 5-6 membered aryl or heteroaryl ring; and
 (d) $R^5$ is R, OR$^7$, or N(R$^7$)$_2$, wherein R is carbocyclic, or an optionally substituted 5 or 6-membered aryl or heteroaryl ring.

More preferred compounds of formula I', or of any of the subformulae II-A', II-B', II-C', III-A', III-B', III-C', IV-A', IV-B', and V-A' are those having one or more, more preferably more than one, and most preferably all, of the features selected from the group consisting of:
 (a) X is —C(O)—;
 (b) $R^3$ is selected from optionally substituted phenyl, methyl, ethyl, propyl, cyclopropyl, N(methyl)$_2$, N(ethyl)$_2$, N(CH$_2$CH$_2$OH)$_2$, pyridinyl, morpholinyl, piperidinyl, piperazinyl, S-methyl, OH, O-methyl, O-ethyl, or —CH$_2$-morpholin-4-yl;
 (c) $T_mR^1$ is selected from optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$; and
 (d) $R^5$ is OH, NH$_2$, carbocyclic, or an optionally substituted phenyl or pyridyl ring.

Another preferred embodiment of this invention relates to compounds of formula I":

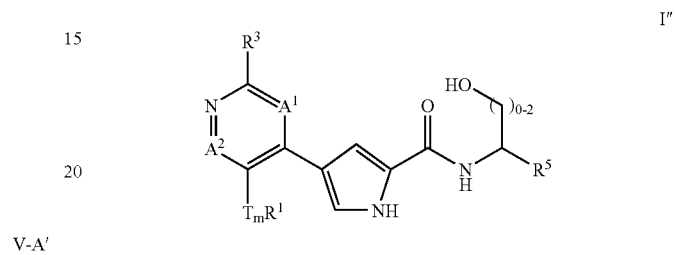

or a pharmaceutically acceptable salt or derivative thereof, wherein:

$A^1$, $A^2$, T, m, $R^1$, $R^3$, and $R^5$ are as described above.

Accordingly, the present invention relates to compounds of formula I" wherein the functional group $R^3$ is attached to the pyrimidine ring via a nitrogen linkage (II-A", II-B", and II-C"), via a sulfur linkage (III-A", III-B", and III-C"), via an oxygen linkage (IV-A" and IV-B"), or is R (V-A") as shown below:

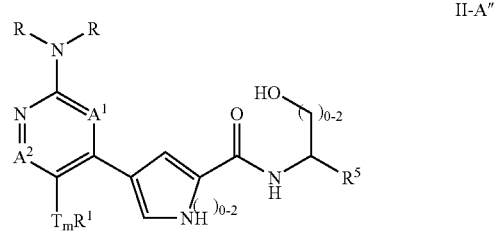

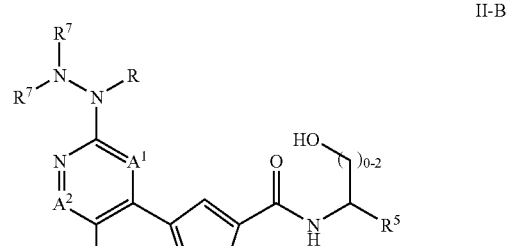

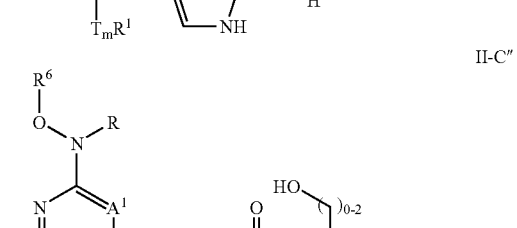

-continued

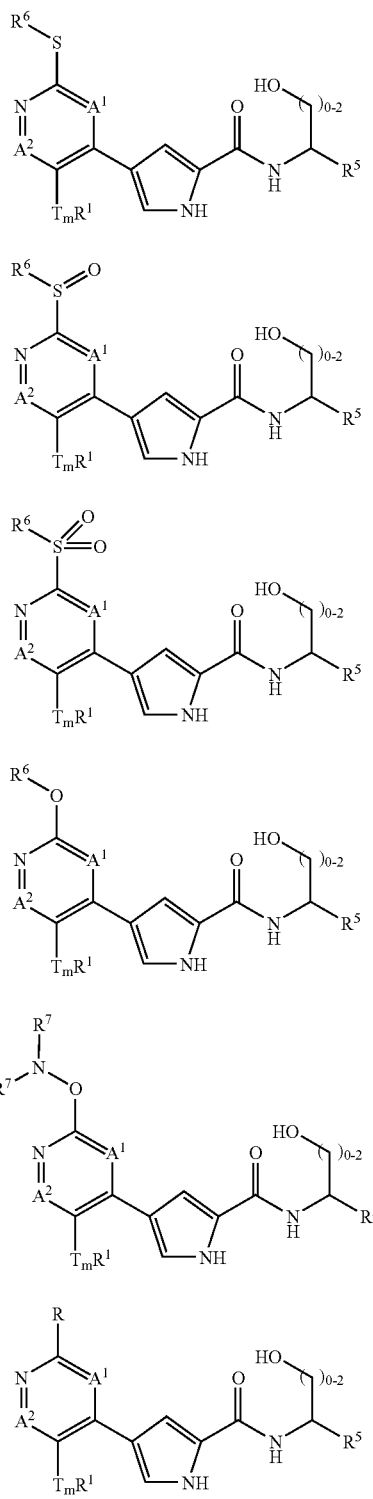

or a pharmaceutically acceptable salt or derivative thereof, wherein $A^1$, $A^2$, $T_mR^1$, R, $R^6$, $R^7$, and $R^5$ are as described above.

Preferred $A^1$, $A^2$, $T_mR^1$ and $R^3$ groups of formula I", or of any of the subformulae II-A", II-B", II-C", III-A", III-B", III-C", IV-A", IV-B", and V-A" are as described above for formula I and subformulae II-A, II-B, II-C, III-A, III-B, III-C, IV-A, IV-B, and V-A.

Preferred $R^5$ groups of formula I", or of any of the subformulae II-A", II-B", II-C", III-A", III-B", III-C", IV-A", IV-B", and V-A" are optionally substituted 6-membered aryl, heteroaryl, and carbocyclic rings, such as phenyl, pyridyl, and cyclohexyl.

Preferred compounds of formula I", or of any of the subformulae II-A", II-B", II-C", III-A", III-B", III-C", IV-A", IV-B", and V-A" are those having one, more preferably more than one, and most preferably all, of the -features selected from the group consisting of:

(a) $R^3$ is —N(optionally substituted $C_{1-6}$ aliphatic)$_2$; —SH; —S($C_{1-6}$ aliphatic); —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;

(b) $T_mR^1$ is hydrogen, $N(R^7)_2$, OH, 3-6 membered carbocyclyl, or an optionally substituted group selected from $C_{1-6}$ aliphatic or a 5-6 membered aryl or heteroaryl ring; and (c) $R^5$ is an optionally substituted 6-membered aryl, heteroaryl, or carbocyclic ring.

More preferred compounds of formula I", II-A", II-B", II-C", III-A", III-B", III-C", IV-A", IV-B", and V-A" are those having one or more, more preferably more than one, and most preferably all, of the features selected from the group consisting of:

(a) $R^3$ is selected from optionally substituted phenyl, methyl, ethyl, propyl, cyclopropyl, N(methyl)$_2$, N(ethyl)$_2$, N(CH$_2$CH$_2$OH)$_2$, pyridinyl, morpholinyl, piperidinyl, piperazinyl, S-methyl, OH, O-methyl, O-ethyl, or —CH$_2$-morpholin-4-yl;

(b) $T_mR^1$ is selected from optionally substituted phenyl, methyl, ethyl, propyl, cyclopropyl, cyclohexyl, CH$_2$OCH$_3$, CH$_2$OH, NH$_2$, NHCH$_3$, NHAc, NHC(O) NHCH$_3$, or CH$_2$NHCH$_3$; and (c) $R^5$ is cyclohexyl or an optionally substituted phenyl or pyridyl ring.

Another preferred embodiment of this invention relates to compounds of formula I°:

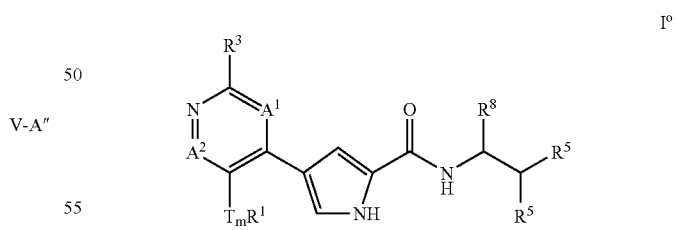

or a pharmaceutically acceptable salt or derivative thereof, wherein:

$A^1$, $A^2$, T, m, $R^1$, $R^3$, $R^5$, and $R^8$ are as described above.

Accordingly, the present invention relates to compounds of formula I° wherein the functional group $R^3$ is attached to the pyrimidine ring via a nitrogen linkage (II-A°, II-B°, and II-C°), via a sulfur linkage (III-A°, III-B°, and III-C°), via an oxygen linkage (IV-A° and IV-B°), or is R (V-A°) as shown below:

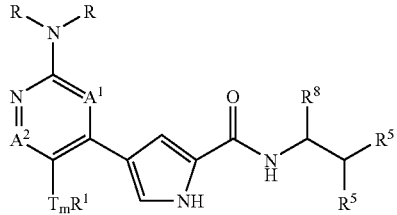
II-A°

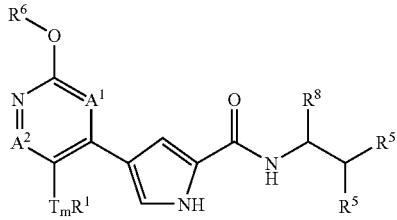
IV-A°

-continued

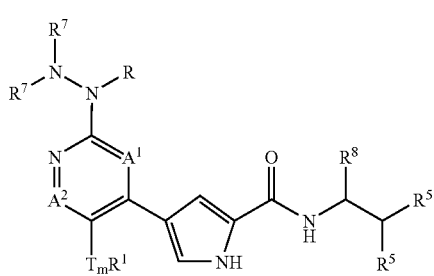
II-B°

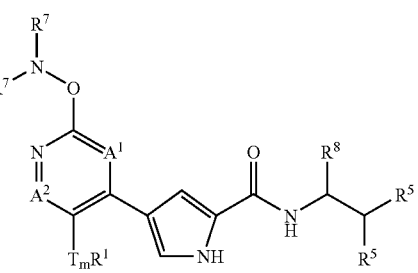
IV-B°

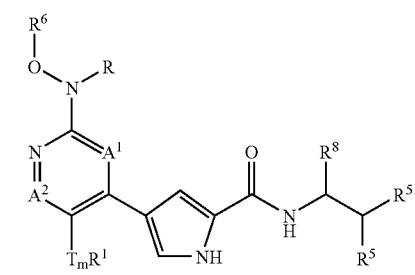
II-C°

V-A°

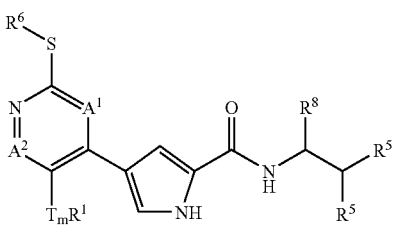
III-A°

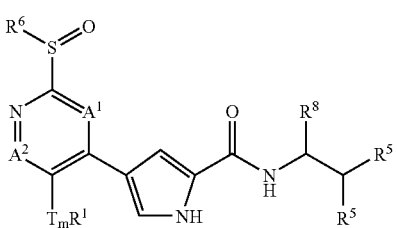
III-B°

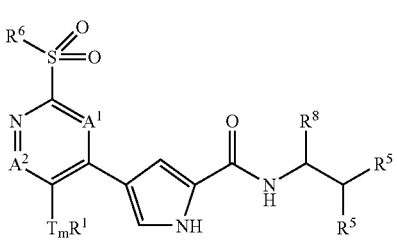
III-C° or a pharmaceutically acceptable salt or derivative thereof, wherein $A^1$, $A^2$, $T_mR^1$, R, $R^6$, $R^7$, $R^5$, and $R^8$ are as described above.

Preferred $R^5$ groups of formula I°, II-A°, II-B°, II-C°, III-A°, III-B°, III-C°, IV-A°, IV-B°, and V-A° are R, $OR^7$ or $N(R^7)_2$. Examples of such groups include OH, $CH_2OH$, $NH_2$, $CH_2NH_2$, $CH_2CH_2NH_2$, carbocyclic, or optionally substituted 5 or 6-membered aryl or heteroaryl rings, such as phenyl, pyridyl, and cyclohexyl. Preferred $R^8$ groups of formula I°, II-A°, II-B°, II-C°, III-A°, III-B°, III-C°, IV-A°, IV-B°, and V-A° are R, —$(CH_2)_wOR^7$ or —$(CH_2)_wN(R^4)_2$ wherein R is an optionally substituted group selected from $C_{1-4}$ aliphatic, 3-6 membered heterocyclic, or a 5-6 membered aryl or heteroaryl ring. Examples of such $R^8$ groups include phenyl, methyl, ethyl, OH, $CH_2OH$, $NH_2$, $CH_2NH_2$, and $CH_2CH_2NH_2$. Preferred substituents on the $R^5$ aryl or heteroaryl ring are halogen, haloalkyl, OR°, and R°.

Preferred $A^1$, $A^2$, $T_mR^1$ and $R^3$ groups of formula I°, or of any of the subformulae II-A°, II-B°, II-C°, III-A°, III-B°, III-C°, IV-A°, IV-B°, and V-A° are as described above for formula I and subformulae II-A, II-B, II-C, III-A, III-B, III-C, IV-A, IV-B, and V-A.

Preferred compounds of formula I°, or of any of the subformulae II-A°, II-B°, II-C°, III-A°, III-B°, III-C°, IV-A°, IV-B°, and V-A° are those having one or more, more preferably more than one, and most preferably all, of the features selected from the group consisting of:

(a) $R^3$ is —N(optionally substituted $C_{1-6}$ aliphatic)$_2$; —SH; —S($C_{1-6}$ aliphatic); —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;

(b) $T_mR^1$ is hydrogen, amino, OH, 3-6 membered carbocyclyl, or an optionally substituted group selected from $C_{1-6}$ aliphatic or a 5-6 membered aryl or heteroaryl ring; and (c) $R^5$ is R, $OR^7$, or $N(R^7)_2$, wherein R is carbocyclic, or an optionally substituted 5 or 6-membered aryl or heteroaryl ring.

More preferred compounds of formula I°, or of any of the subformulae II-A°, II-B°, II-C°, III-A°, III-B°, III-C°, IV-A°, IV-B°, and V-A° are those having one or more, more preferably more than one, and most preferably all, of the features selected from the group consisting of:

(a) $R^3$ is selected from optionally substituted phenyl, methyl, ethyl, propyl, cyclopropyl, N(methyl)$_2$, N(ethyl)$_2$, N(CH$_2$CH$_2$OH)$_2$, pyridinyl, morpholinyl, piperidinyl, piperazinyl, S-methyl, OH, O-methyl, O-ethyl, or —CH$_2$-morpholin-4-yl;

(b) $T_mR^1$ is selected from optionally substituted phenyl, methyl, ethyl, propyl, cyclopropyl, cyclohexyl, CH$_2$OCH$_3$, CH$_2$OH, OH, NH$_2$, NHCH$_3$, NHAc, NHC(O)NHCH$_3$, or CH$_2$NHCH$_3$; and (c) $R^5$ is OH, CH$_2$OH, NH$_2$, CH$_2$NH$_2$, CH$_2$CH$_2$NH$_2$, carbocyclic, or an optionally substituted phenyl or pyridyl ring.

In another embodiment, the present invention relates to compounds of formula (Ia), (Ib), (Ic), and (Id):

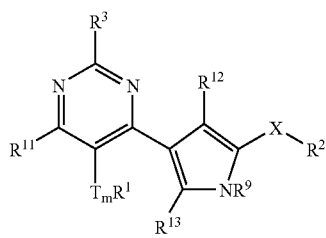
(Ia)

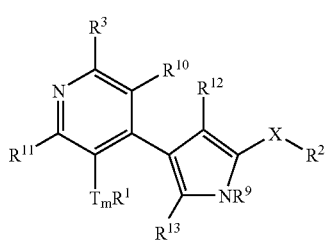
(Ib)

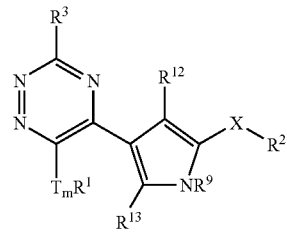
(Ic)

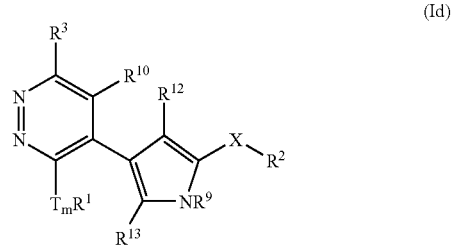
(Id)

or a pharmaceutically acceptable salt or derivative thereof, wherein $T_mR^1$, X, $R^2$, $R^3$, $R^9$, $R^{10}$, $R^{11}$, $R^{12}$, and $R^{13}$ are as described above.

Preferred $T_mR^1$, X, $R^2$, $R^3$, $R^9$, $R^{10}$, $R^{11}$, $R^{12}$, and $R^{13}$ groups of formula (Ia), (Ib), (Ic), and (Id) are as described above for formula I or of any of the subformulae II-A, II-B, II-C, III-A, III-B, III-C, IV-A, IV-B, and V-A.

According to another preferred embodiment, the present invention relates to compounds of formula (Ib), wherein $R^3$ is an optionally substituted 5-6 membered saturated, partially saturated, or aromatic ring having 0-2 heteroatoms independenlty selected from nitrogen, oxygen, or sulful. More preferred are compounds of formula (Ib) wherein $R^3$ is an optionally substituted phenyl or pyridyl.

Preferred compounds of formula I wherein $A^1$ is N, $A^2$ is CH, X is —C(O)—, $R^9$, $R^{12}$, and $R^{13}$ are hydrogen are set forth in Table 1 below. More preferred compounds of formula I are those of formula I', III" or I°.

TABLE 1

Compounds of Formula I

| No. I- | $R^3$ | $T_mR^1$ | $R^2$ |
|---|---|---|---|
| 1 | morpholin-4-yl | Methyl | naphthalen-1-ylmethyl-HN— |

TABLE 1-continued
Compounds of Formula I
| No. I- | R³ | T_mR¹ | R² |
|---|---|---|---|
| 2 | 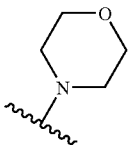 | Methyl | 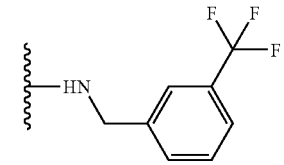 |
| 3 | 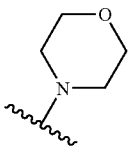 | Methyl | 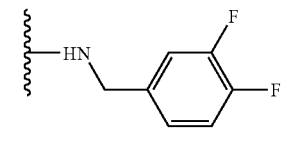 |
| 4 | 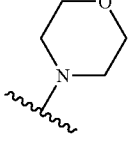 | 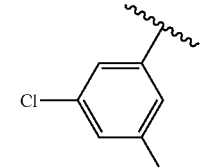 | 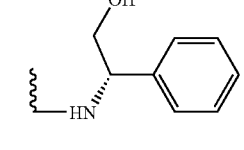 |
| 5 | 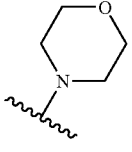 | 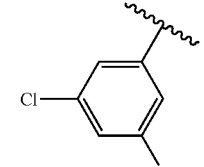 | 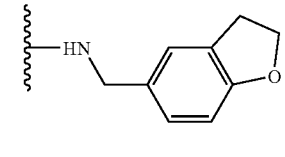 |
| 6 | 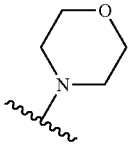 | 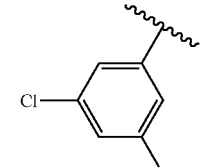 | 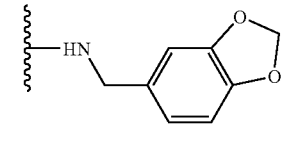 |
| 7 | 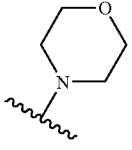 | Methyl | 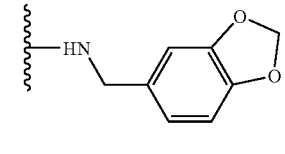 |
| 8 | 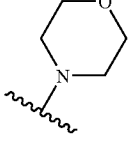 | 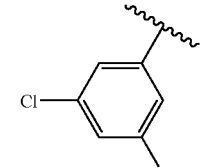 | 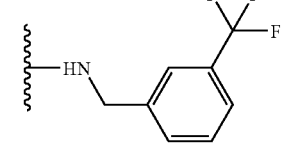 |
| 9 | 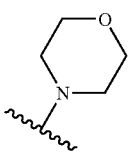 | 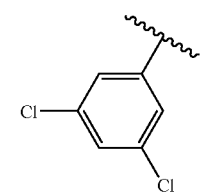 | 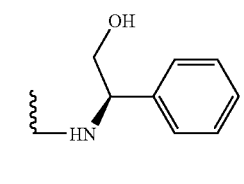 |

TABLE 1-continued
Compounds of Formula I
| No. I- | R³ | T_mR¹ | R² |
|---|---|---|---|
| 10 | 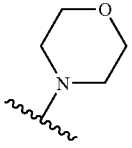 | 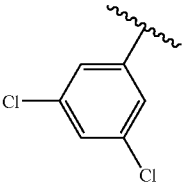 | 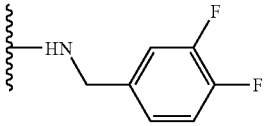 |
| 11 | 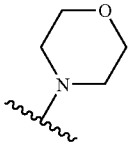 | 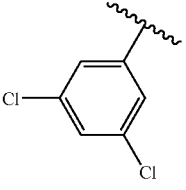 | 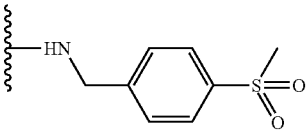 |
| 12 | 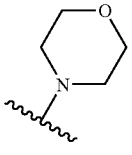 | 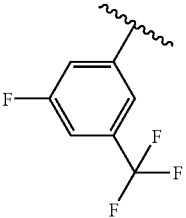 | 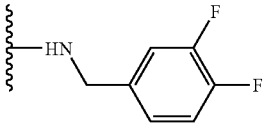 |
| 13 | 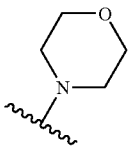 | 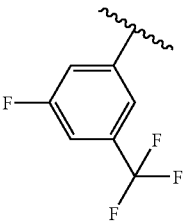 | 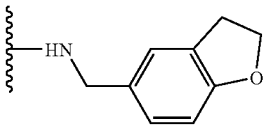 |
| 14 | 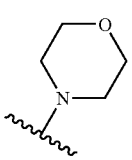 | 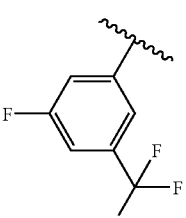 | 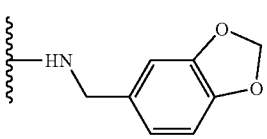 |
| 15 | 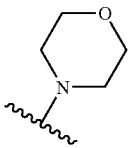 | 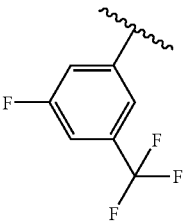 | 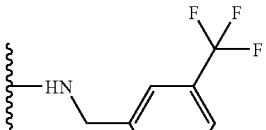 |

TABLE 1-continued
Compounds of Formula I
| No. I- | R³ | T_mR¹ | R² |
|---|---|---|---|
| 16 | 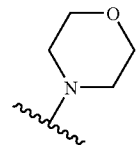 | 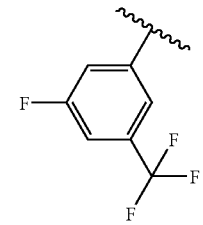 | 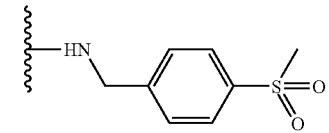 |
| 17 | 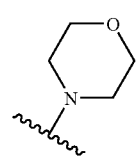 | 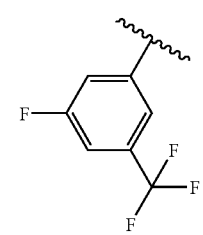 | 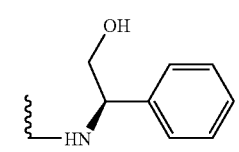 |
| 18 | 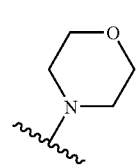 | Methyl | 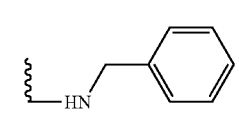 |
| 19 | 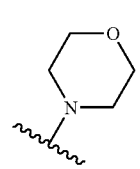 | Methyl | 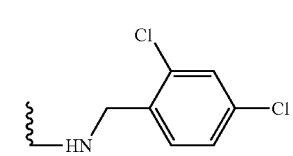 |
| 20 | 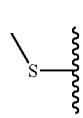 | Methyl | 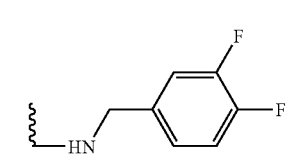 |
| 21 | 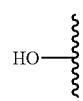 | Methyl | 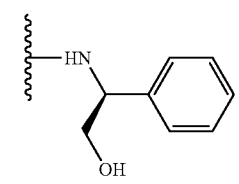 |
| 22 | 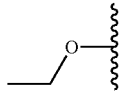 | Methyl | 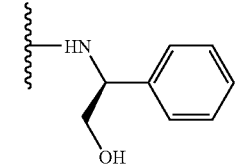 |
| 23 |  | Methyl | 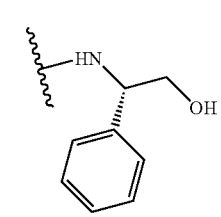 |

TABLE 1-continued
Compounds of Formula I
| No. I- | R³ | TₘR¹ | R² |
|---|---|---|---|
| 24 | 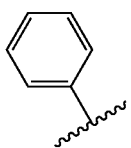 | Methyl | 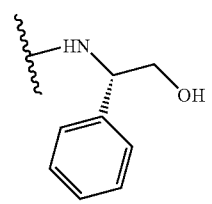 |
| 25 | methyl | methyl | 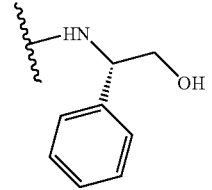 |
| 26 | 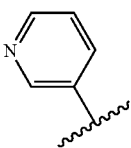 | Methyl | 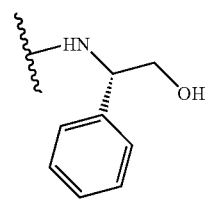 |
| 27 | 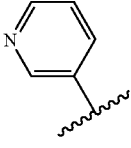 | —CH₂OH | 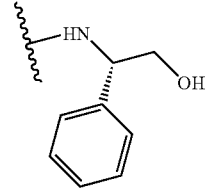 |
| 28 |  | Methyl | 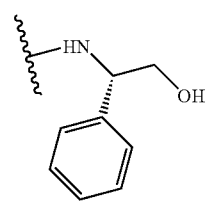 |
| 29 | 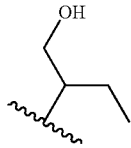 | —CH₂OH | 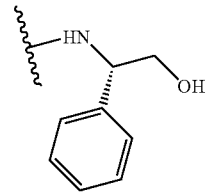 |
| 30 | 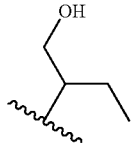 | —CH₂OH | 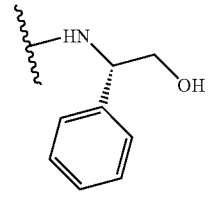 |

TABLE 1-continued

Compounds of Formula I

| No. I- | R³ | TₘR¹ | R² |
|---|---|---|---|
| 31 | 2-ethyl-hydroxymethyl group | —CH₂NH₂ | (R)-2-hydroxy-1-phenylethylamino |
| 32 | morpholino | Methyl | 1-(3-chlorophenyl)-2-aminoethylamino |
| 33 | morpholino | methyl | 1-(3-chlorophenyl)-3-aminopropylamino |
| 34 | morpholino | H | 1-(3-chlorophenyl)-2-aminoethylamino |
| 35 | morpholino | H | 1-(3-chlorophenyl)-3-aminopropylamino |
| 36 | morpholino | N-(2-chloro-5-substituted-benzyl)-3-hydroxy-2-methylpropanamide | pyridin-4-ylmethylamino |
| 37 | morpholino | N-(2-chloro-5-substituted-benzyl)-3-hydroxy-2-methylpropanamide | 2-chlorobenzylamino |

TABLE 1-continued

Compounds of Formula I

| No. I- | R³ | TₘR¹ | R² |
|---|---|---|---|
| 38 | morpholine (N-linked) | HO-CH₂-CH(CH₃)-C(=O)-NH-CH₂-(2-Cl,5-linked phenyl) | -NH-CH(3-Cl-phenyl)-CH₂-NH₂ |
| 39 | morpholine (N-linked) | HO-CH₂-CH(CH₃)-C(=O)-NH-CH₂-(2-Cl,5-linked phenyl) | -NH-CH(3-Cl-phenyl)-CH₂-CH₂-NH₂ |
| 40 | morpholine (N-linked) | MeO-CH₂-CH(NH₂)-C(=O)-NH-CH₂-(2-Cl,5-linked phenyl) | -NH-CH₂-(4-pyridyl) |
| 41 | morpholine (N-linked) | MeO-CH₂-CH(NH₂)-C(=O)-NH-CH₂-(2-Cl,5-linked phenyl) | -NH-CH₂-(2-Cl-phenyl) |
| 42 | morpholine (N-linked) | MeO-CH₂-CH(NH₂)-C(=O)-NH-CH₂-(2-Cl,5-linked phenyl) | -NH-CH(3-Cl-phenyl)-CH₂-NH₂ |
| 43 | morpholine (N-linked) | MeO-CH₂-CH(NH₂)-C(=O)-NH-CH₂-(2-Cl,5-linked phenyl) | -NH-CH(3-Cl-phenyl)-CH₂-CH₂-NH₂ |
| 44 | morpholine-N-CH₂-CH₂- | H | -N(CH₃)-CH(CH₃)-CH(OH)-phenyl |

TABLE 1-continued
Compounds of Formula I
| No. I- | R³ | T_mR¹ | R² |
|---|---|---|---|
| 45 | 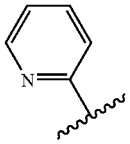 | H | 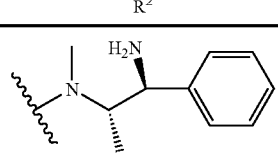 |
Additional preferred compounds of Formula I wherein $A^2$ is CH, X is —C(O)—, and $R^{13}$ is hydrogen are set forth in Table 2 below.
TABLE 2
Additional compounds of Formula I
| No. I- | A¹ | R³ | T_mR¹ | R⁹ | R¹² | R² |
|---|---|---|---|---|---|---|
| 46 | N | —SCH₃ | Methyl | H | H | 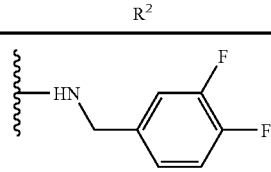 |
| 47 | N | 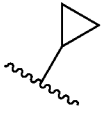 | Methyl | H | H | 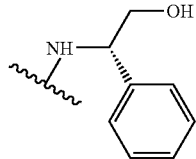 |
| 48 | N | 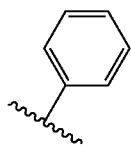 | Methyl | H | H | 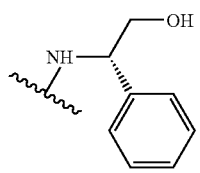 |
| 49 | N | Methyl | Methyl | H | H | 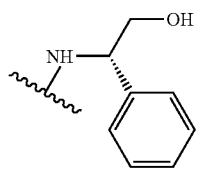 |
| 50 | N | —OH | Methyl | H | H | 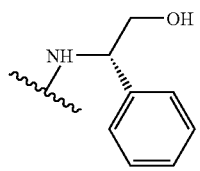 |
| 51 | N | 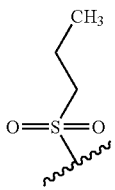 | Methyl | H | H | 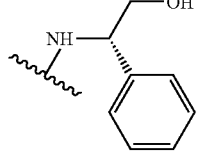 |

TABLE 2-continued
Additional compounds of Formula I
| No. I- | A¹ | R³ | T_mR¹ | R⁹ | R¹² | R² |
|---|---|---|---|---|---|---|
| 52 | N | 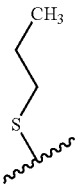 | Methyl | H | H | 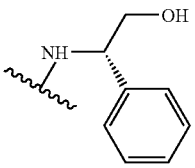 |
| 53 | N | 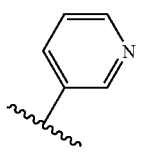 | Methyl | H | H | 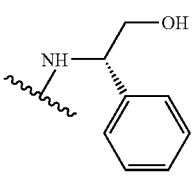 |
| 54 | N | 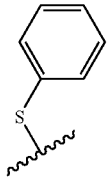 | Methyl | H | H | 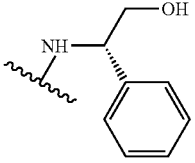 |
| 55 | N | 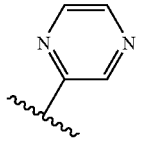 | Methyl | H | H | 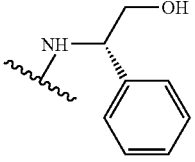 |
| 56 | N | 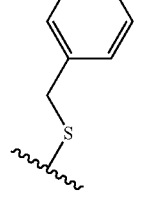 | Methyl | H | H | 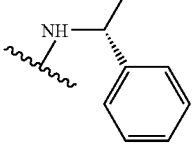 |
| 57 | N | 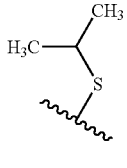 | Methyl | H | H | 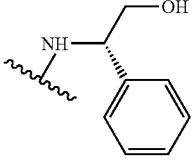 |
| 58 | N | 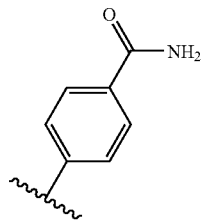 | Methyl | H | H | 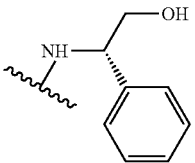 |

TABLE 2-continued

Additional compounds of Formula I

| No. I- | A$^1$ | R$^3$ | T$_m$R$^1$ | R$^9$ | R$^{12}$ | R$^2$ |
|---|---|---|---|---|---|---|
| 59 | N | 4-methylphenyl | Methyl | H | H | NH-CH(CH$_2$OH)-phenyl |
| 60 | CH | (CH$_3$)$_2$N-N(CH$_3$)- | Methyl | H | H | NH-CH(CH$_2$OH)-(3-CF$_3$-phenyl) |
| 61 | CH | (CH$_3$)$_2$N-N(CH$_3$)- | Methyl | H | H | NH-CH(CH$_2$OH)-(3-CH$_3$-phenyl) |
| 62 | CH | (CH$_3$)$_2$N-N(CH$_3$)- | Cl | H | H | NH-CH(CH$_2$OH)-phenyl |
| 63 | CH | CH$_3$C(O)-N(CH$_3$)-N(CH$_3$)- | Cl | H | H | NH-CH(CH$_2$OH)-phenyl |
| 64 | CH | HO-CH$_2$CH$_2$-O-N(CH$_3$)- | Cl | H | H | NH-CH(CH$_2$OH)-(3-Cl-4-F-phenyl) |
| 65 | N | HO-CH$_2$CH$_2$-O-N(CH$_3$)- | Cl | CF$_3$ | H | NH-CH(CH$_2$OH)-(3-Cl-4-F-phenyl) |

TABLE 2-continued

Additional compounds of Formula I

| No. I- | A¹ | R³ | T_mR¹ | R⁹ | R¹² | R² |
|---|---|---|---|---|---|---|
| 66 | CH | HO—CH₂CH₂—O—N(CH₃)— | Cl | Methyl | H | —NH—CH(CH₂OH)—(3-Cl,4-F-phenyl) |
| 67 | CH | (CH₃)₂N—N(CH₃)— | H | H | Methyl | —NH—CH(CH₂OH)—(3-Cl-phenyl) |
| 68 | CH | phenyl | methyl | H | H | —NH—CH(CH₂OH)—(3-Cl-phenyl) |

Additional preferred compounds of formula I wherein A¹ is C—R¹⁰, and the R³ and C—R¹⁰ groups are taken together to form an optionally substituted ring are set forth in Table 3 below.

TABLE 3

Additional compounds of Formula I

| No. I- | Structure |
|---|---|
| 69 | 1-methyl-7-azaindol-4-yl pyrrole-2-carboxamide with NH-CH(CH₂OH)-phenyl |
| 70 | 1-methyl-7-azaindol-4-yl pyrrole-2-carboxamide with NH-CH(CH₂OH)-(3-methylphenyl) |
| 71 | 1-methyl-5-methyl-7-azaindol-4-yl pyrrole-2-carboxamide with NH-CH(CH₂OH)-phenyl |
| 72 | 1-methyl-7-azaindol-4-yl pyrrole-2-carboxamide with NH-CH(CH₂OH)-(2,3-difluorophenyl) |

TABLE 3-continued

Additional compounds of Formula I

| No. I- | Structure |
|---|---|
| 73 | 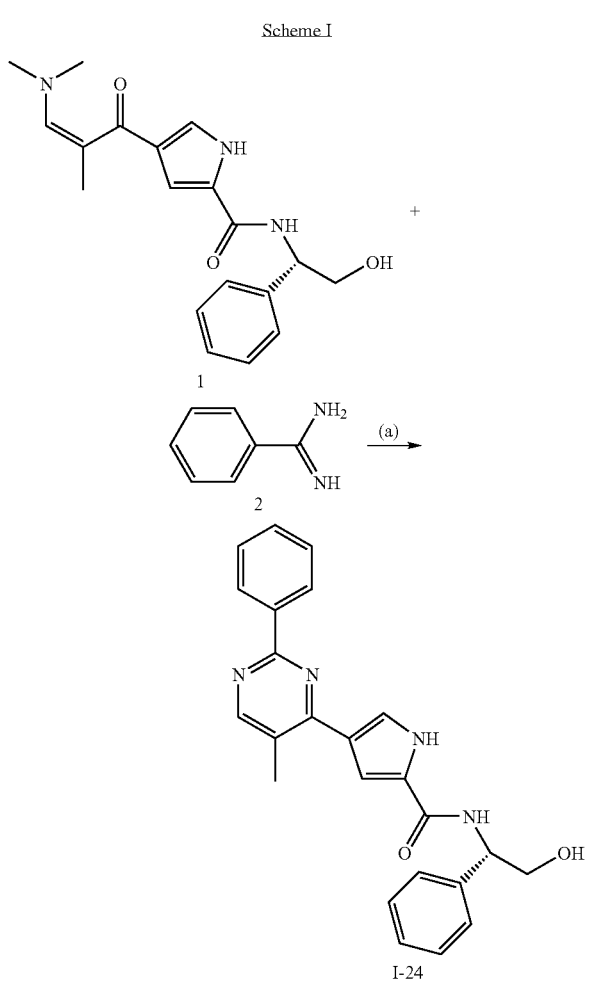 |

The present compounds may be prepared in general by methods known to those skilled in the art for analogous compounds, as illustrated by Schemes I and II and the synthetic examples shown below.

Scheme I

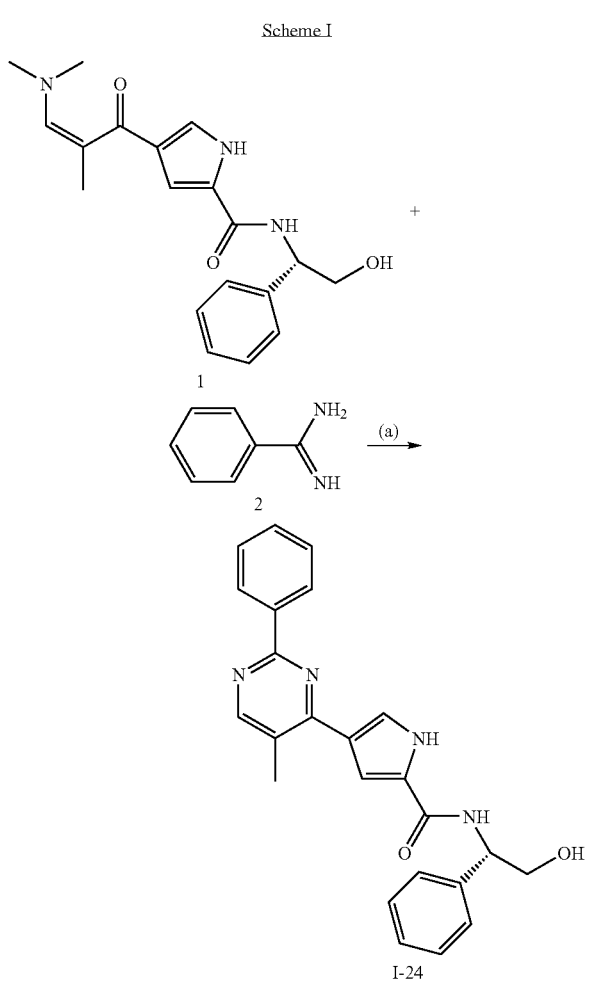

Reagents and conditions:
(a) K$_2$CO$_3$, DMA, 100° C., 48 hours.

Using the preparation of compound I-24 to illustrate, Scheme I above shows a general synthetic route that is used for preparing compounds of formula I wherein R$^3$ is R. The formation of the pyrimidine compound I-24 at step (a) is achieved by the treatment of enamine 1 with an amidine 2 at elevated temperature. One of skill in the art will recognize that Scheme I can also be used to prepare analogous compounds of formula I wherein R$^3$ is other than R.

Scheme II

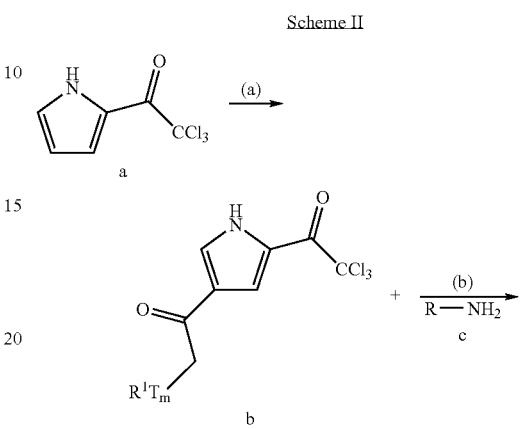

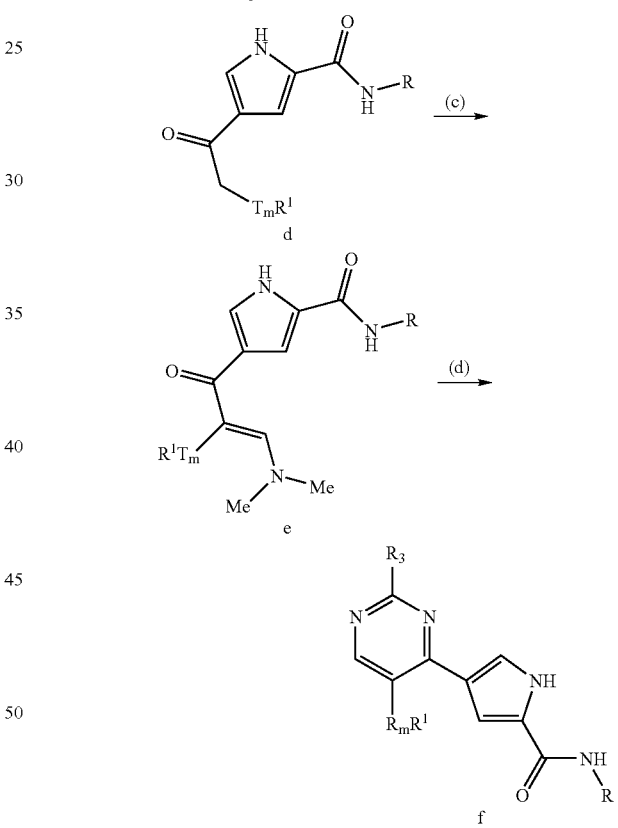

Reagents and conditions:
(a) T$_m$R$^1$CH$_2$COCl, AlCl$_3$, CH$_2$Cl$_2$, 2 hours, room temperature;
(b) DMF, 24 hours, room temperature;
(c) (Me$_2$N)$_2$—CHOt-Bu, THF 24 hours, room temperature; and
(d) amidine, hydroxylamine based guanidine or alkyl thiourea in EtOH or MeCN or DMA, 70-100° C.

Scheme II above shows a general synthetic route that is used for preparing the compounds of formula I of this invention when X is —C(O)— and R$^2$ is —N(R)$_2$. In step (a), an optionally substituted acid chloride is combined with compound a, dichloromethane, and aluminum trichloride to form compound b. In cases where benzoyl acid chlorides are used, a wide variety of substituents on the phenyl ring are amenable to this reaction. Aliphatic acid chlorides are also used in many cases. Examples of suitable $R^2$ groups include, but are not limited to, those set forth in Table 1 above.

The formation of amide d is achieved by treating compound b with an amine c in DMF. When amine c is a primary amine, the reaction proceeds at ambient temperature. When amine c is a secondary amine, the reaction is heated at 50° C. to achieve complete reaction and afford amide d.

The formation of enamine e at step (c) is achieved by treating amide d with $(Me_2N)_2$—CHOt-Bu at ambient temperature. Alternatively, the reaction to form enamine e at step (c) is also achieved by using dimethylformamide-dimethylacetal (DMF-DMA). The reaction using DMF-DMA typically requires elevated temperature to afford enamine e whereas using $(Me_2N)_2$—OtBu has the advantage of proceeding at ambient temperature to afford the enamine e in higher purity.

The formation of the pyrimidine compound f at step (d) is achieved by the treatment of enamine e with an amidine or appropriately substituted guanidine at elevated temperature. As an alternative method, in step (e) intermediate e may be cyclized with S-methyl thiourea to form the 2-thiomethylpyrimidine.

The compounds of formula I synthesized by this method, as exemplified in Table 1, were isolated by preparatory HPLC (reverse phase, 10→90% MeCN in water over 15 minutes). The details of the conditions used for producing these compounds are set forth in the Examples.

The activity of a compound utilized in this invention as an inhibitor of ERK, CDK2, Aurora2, GSK3, AKT3, or ROCK may be assayed in vitro, in vivo or in a cell line according to methods known in the art. In vitro assays include assays that determine inhibition of either the phosphorylation activity or ATPase activity of activated ERK, CDK2, Aurora2, GSK3, AKT3, or ROCK. Alternate in vitro assays quantitate the ability of the inhibitor to bind to ERK or to CDK2, Aurora2, GSK3, AKT3, or ROCK. Inhibitor binding may be measured by radiolabelling the inhibitor prior to binding, isolating the inhibitor/ERK, inhibitor/CDK2, inhibitor/Aurora2, inhibitor/GSK3, inhibitor/AKT3, or inhibitor/ROCK complex and determining the amount of radiolabel bound. Alternatively, inhibitor binding may be determined by running a competition experiment where new inhibitors are incubated with ERK, CDK2, Aurora2, GSK3, AKT3, or ROCK bound to known radioligands. Detailed conditions for assaying a compound utilized in this invention as an inhibitor of ERK, CDK2, Aurora2, GSK3, AKT3, or ROCK kinase are set forth in the Examples below.

According to another embodiment, the invention provides a composition comprising a compound of this invention or a pharmaceutically acceptable derivative thereof and a pharmaceutically acceptable carrier, adjuvant, or vehicle.

According to another embodiment, the amount of the compound in the compositions of this invention is such that is effective to detectably inhibit a protein kinase, particularly ERK, CDK2, Aurora2, GSK3, AKT3, or ROCK in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "detectably inhibit", as used herein means a measurable change in ERK, CDK2, Aurora2, GSK3, AKT3, or ROCK activity between a sample comprising said composition and an ERK, CDK2, Aurora2, GSK3, AKT3, or ROCK kinase and an equivalent sample comprising ERK, CDK2, Aurora2, GSK3, AKT3, or ROCK kinase in the absence of said composition. According to a preferred embodiment, inhibition of kinase activity by a composition according to the present invention is greater than 10% compared to the kinase activity in the absence of the composition. Preferably, inhibition is greater than 20%, 30%, or 40%, and even more preferably greater than 50%, 60%, 70%, 80%, or 90%.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques.

Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents the compounds of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating Alzheimer's disease (such as Aricept®), agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguamides, and insulin sensitizers; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

According to another embodiment, the invention relates to a method of inhibiting ERK, CDK2, Aurora2, GSK3, AKT3, or ROCK kinase activity in a biological sample comprising the step of contacting said biological sample with a compound of this invention, or a pharmaceutically acceptable composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ERK, CDK2, Aurora2, GSK3, AKT3, or ROCK kinase activity in a biological sample is useful for a variety of purposes that are known to one of skill in the art. Examples of such purposes include, but are not limited to, blood transfusion, organ-transplantation, biological specimen storage, and biological assays.

According to another embodiment, the invention provides a method for treating or lessening the severity of an ERK-, CDK2-, Aurora2-, GSK3-, AKT3-, or ROCK-mediated disease or condition in a patient comprising the step of administering to said patient a pharmaceutically acceptable composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

The term "CDK-2-mediated condition" or "disease", as used herein, means any disease or other deleterious condition in which CDK-2 is known to play a role. The term "CDK-2-mediated condition" or "disease" also means those diseases or conditions that are alleviated by treatment with a CDK-2 inhibitor. Such conditions include, without limitation, cancer, Alzheimer's disease, restenosis, angiogenesis, glomerulonephritis, cytomegalovirus, HIV, herpes, psoriasis, atherosclerosis, alopecia, and autoimmune diseases such as rheumatoid arthritis. See Fischer, P. M. and Lane, D. P., *Current Medicinal Chemistry,* 7, 1213-1245 (2000); Mani, S., Wang, C., Wu, K., Francis, R. and Pestell, R., *Exp. Opin. Invest. Drugs,* 9, 1849 (2000); Fry, D. W. and Garrett, M. D., *Current Opinion in Oncologic, Endocrine & Metabolic Investigational Drugs,* 2, 40-59 (2000).

The term "Aurora-2-mediated condition" or "disease", as used herein, means any disease or other deleterious condition in which Aurora is known to play a role. The term "Aurora-2-mediated condition" or "disease" also means those diseases or conditions that are alleviated by treatment with an Aurora-2 inhibitor. Such conditions include, without limitation, cancer. The term "cancer" includes, but is not limited to the following cancers: colon, breast, stomach, and ovarian.

The term "GSK-3-mediated condition" or "disease", as used herein, means any disease or other deleterious condition or state in which GSK-3 is known to play a role. Such diseases or conditions include, without limitation, diabetes, neurodegenerative disorders, Alzheimer's disease, Huntington's Disease, Parkinson's Disease, AIDS-associated dementia, amyotrophic lateral sclerosis (AMS), multiple sclerosis (MS), schizophrenia, cardiomycete hypertrophy, reperfusion/ischemia, stroke, and baldness.

One aspect of this invention relates to a method of enhancing glycogen synthesis and/or lowering blood levels of glucose in a patient in need thereof, which method comprises administering to the patient a therapeutically effective amount of a compound of formula I or a pharmaceutically acceptable thereof. This method is especially useful for diabetic patients. Another method relates to inhibiting the production of hyperphosphorylated Tau protein, which is useful in halting or slowing the progression of Alzheimer's disease. Another method relates to inhibiting the phosphorylation of β-catenin, which is useful for treating schizophrenia.

The terms "AKT3-mediated condition" or "disease", as used herein, mean any disease state or other deleterious condition in which AKT3 is known to play a role. The terms "AKT3-mediated disease" or "AKT3-mediated condition" also mean those diseases or conditions that are alleviated by treatment with an AKT inhibitor. AKT3-mediated diseases or conditions include, but are not limited to, proliferative disorders, cancer, and neurodegenerative disorders. The association of AKT3 with various diseases has been described [Zang, Q. Y., et al, *Oncogene,* 19 (2000)] and [Kazuhiko, N., et al, *The Journal of Neuroscience,* 20 (2000)].

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, arteriosclerosis, spasm, retinopathy, inflammatory disorders, autoimmune disorders, AIDS, and osteoporosis.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121; the contents of which are incorporated herein by reference in their entirety. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may be further covered by a suitable topcoat of fluorosilicone, polysaccharides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

SYNTHETIC EXAMPLES

For compounds where the HPLC Method is designated as "A", the following method was utilized: a gradient of water:MeCN, 0.1% TFA (95:5→0:100) was run over 22 minutes at 1 mL/min and 214 nm. For compounds where the HPLC Method is designated as "B", the following method was utilized: a gradient of water:MeCN, 0.1% TFA (90:10→0:100) was run over 8 minutes at 1 mL/min and 214 nm. Each of methods A and B utilized the YMC ODS-AQ 55 120A column with a size of 3.0×150 mm. As used herein, the term "$R_t$" refers to the retention time, in minutes, associated with the compound using the designated HPLC method.

Example 1

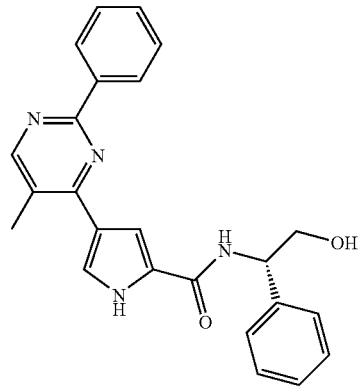

I-24

4-(5-Methyl-2-phenyl-pyrimidin-4-yl)-1H-pyrrole-2 carboxylic acid (2-hydroxy-1-(S)-phenyl-ethyl)-amide (1-24): To a solution of 4-(3-dimethylamino-2-methoxymethyl-acryloyl)-1H-pyrrole-2-carboxylic acid (2-hydroxy-1-(S)-phenyl-ethyl)-amide (0.72 mmol, 260 mg) in DMA (5 mL) was added phenyl amidine.HCl (1.5 mmol, 240 mg) and potassium carbonate (2.3 mmol, 315 mg). The reaction mixture was stirred for 48 hours at 100° C. The solvent was removed under hi-vacuum "GeneVac". Purification by prep HPLC (Gilson: Column=CombiHT SB-C 189 5 μM 21.2 mm×100 mm, eluent=0.1% TFA MeCN/H$_2$O gradient) afforded compound I-24 as a pale yellow solid (2.3 mg). HPLC Method B, $R_t$=5.45 minutes; LCMS 399.1 (M+1), 397.2 (M−1); ⁻H NMR consistent with structure.

Example 2

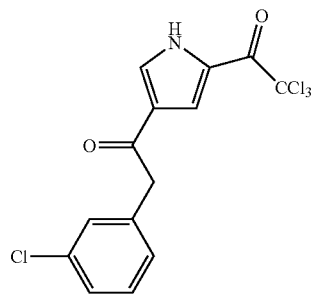

1

2,2,2-Trichloro-1-(4-(3-Chlorophenyl) acetyl-1H-pyrrol-2-yl)-ethanone (1): In a dry flask, 3-chlorophenylacetyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided the title compound 1. HPLC Method A, $R_t$=15 minutes.

Example 3

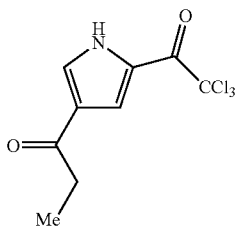

2

1-[5-(2,2,2-Trichloro-acetyl)-1H-pyrrol-3-yl)-propan-1-one 2: In a dry flask, 3-proprionyl chloride (1 equivalent) was combined with 2-trichloroacetyl pyrrole (1 equivalent) in a minimum amount of dichloromethane (DCM). To the resulting solution, at ambient temperature, was added aluminum trichloride (1 equivalent). After 2 hours, the reaction mixture was applied directly onto a silica gel column. Gradient elution with 10% ethyl acetate to 50% ethyl acetate in hexanes provided the title compound 2.

Example 4

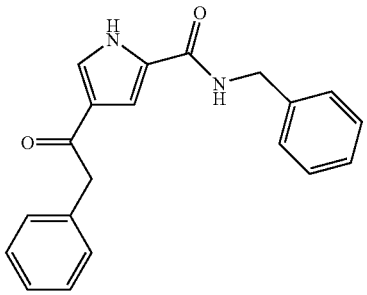

3

4-Phenylacetyl-1H-pyrrole-2-carboxylic acid benzylamide (D3: To a solution of 2,2,2-trichloro-1-(4-phenylacetyl-1H-pyrrol-2-yl)-ethanone (1 equivalent) in DMF, at ambient temperature, was added benzylamine (1.2 equivalents). After 24 hours, the solvent was evaporated and the crude product 3 was used without purification. HPLC Method B, $R_t$=3.8 minutes; FLVMS (M+1) 319.3, (M–1) 317.2.

Example 5

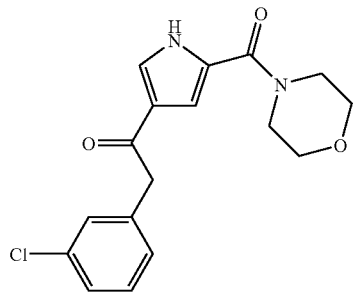

4

2-(3-Chlorophenyl)1-[5-(morpholine-4-carbonyl)-1H-pyrrol-3-yl]-ethanone (4): To a solution of compound 1 (1 equivalent) in DMF, at ambient temperature, was added morpholine (1.2 equivalents). After 24 hours, the solvent was evaporated and the crude product 4 was used without purification. FIA/MS (M+1) 333.3, (M–1) 331.2; $^1$H NMR was consistent with expected structure.

Example 6

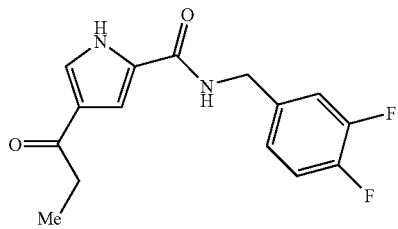

5

4-Propionyl-1H-pyrrole-2-carboxylic acid 3,4-difluorobenzylamide (5): To a solution of compound 2 (1 equivalent) in DMF, at ambient temperature, was added 3,4-difluorobenzyl amine (1.2 equivalents). After 24 hours, the solvent was evaporated and the crude product 5 was used without purification.

Example 7

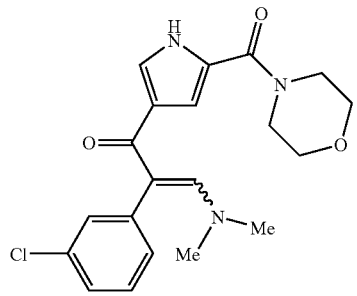

6

2-(3-Chloro-phenyl)-3-dimethylamino-1-[5-(morpholine-4-carbonyl)-1H-pyrrol-3-yl]-propenone (6): To a solution of compound 4 (1 equivalent) in THF, at ambient temperature, was added (Me$_2$N)$_2$CHOt-Bu (3 equivalents). After 24 hours, the solvent was evaporated and the crude product 6 was used without purification. HPLC Method B, $R_t$=11.2 minutes.

Example 8

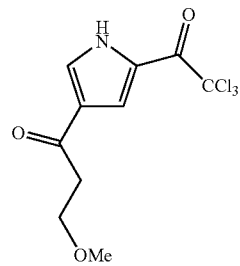

7

3-Methoxy-1-[5-(2,2,2-trichloro-acetyl)-1H-pyrrol-3-yl]-propan-1-one (7): To a solution of 2-trichloroacetyl pyrrole (1.0 equivalent, 4.67 g, 22 mmol) in methylene chloride (5 mL) was added 3-methoxypropionyl chloride (1.0 equivalent, 22 mmol), then aluminium trichloride (1.0 equivalent, 2.93 g, 22 mmol) was added in small portions. After 2.5 hours, the crude mixture was chromatographed on silica gel (MeOH 2% in DCM) to afford 3.0 g of the Friedel-Craft product 7. $^1$H NMR consistent with structure.

Example 9

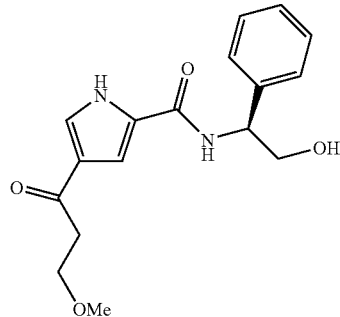

8

4-(3-Methoxy-propionyl)-1H-pyrrole-2-carboxylic acid (2-hydroxy-1-(S)-phenyl-ethyl)-amide (8): To a solution of 3-methoxy-1-[5-(2,2,2-trichloro-acetyl)-1H-pyrrol-3-yl]-propan-1-one (3.0 g, 10 mmol) in acetonitrile (50 mL), cooled to 0° C., was added (S)-(+)-phenyl glycinol (1.2 equivalent, 1.65 g, 12 mmol) and the resulting mixture stirred for 3 days at room temperature. The solvent was removed under reduced pressure and the residue was purified by chromatography on silica gel (MeOH 5% in DCM) to afford 5.3 g of the title compound (8) as a white solid. HPLC Method B, Rt=4.2 minutes; LC/MS(m/z) 317.03 (M+1), 315.00 (M−1); $^1$H NMR consistent with structure.

Example 10

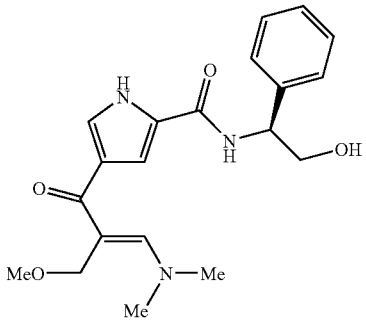

9

4-(3-Dimethylamino-2-methoxymethyl-acryloyl)-1H-pyrrole-2-carboxylic acid (2-hydroxy-1-(S)-phenyl-ethyl)-amide (9): 4-(3-Methoxy-propionyl)-1H-pyrrole-2-carboxylic acid (2-hydroxy-1-(S)-phenyl-ethyl)-amide was treated with an excess of Bredereck's reagent in THF at room temperature to 50° C. for 3 days. The solvent was removed under reduced pressure and the concentrate was used directly in the next step. HPLC Method B, $R_t$=5.0 minutes "broad peak".

Example 11

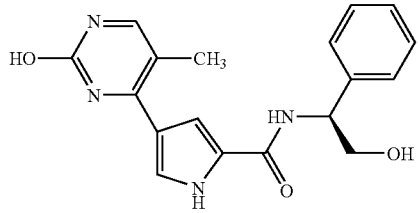
I-21

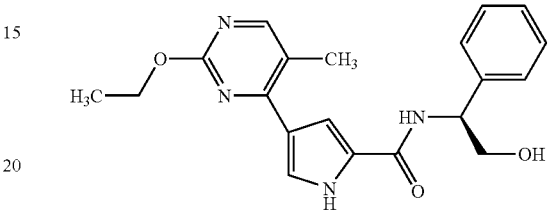
I-22

4-(5-Methyl-2-hydroxy-pyrimidin-4-yl)-1H-pyrrole-2 carboxylic acid (2-hydroxy-1-(S)-phenyl-ethyl)-amide (1-21) and 4-(5-methyl-2-ethoxy-pyrimidin-4-yl)-1H-pyrrole-2 carboxylic acid (2-hydroxy-1-(S)-phenyl-ethyl)-amide (1-22): To a solution of 4-(5-methyl-2-propylsulfone-pyrimidin-4-yl)-1H-pyrrole-2 carboxylic acid (2-hydroxy-1-(S)-phenyl-ethyl)-amide (0.1 mmol, 48 mg) in C$_2$H$_5$OH (1 mL) was added 30% NaOH solution (1 mL). The reaction mixture was stirred for 1 hour at 70° C. The reaction mixture was concentrated in vacuo and purified from prep. HPLC (Gilson: Column=CombiHT SB-C189 5 M 21.2 mm×100 mm, eluent=0.1% TFA MeCN/H$_2$O gradient) afforded compound I-21 as a pale yellow solid (12 mg) and compound I-22 as a yellow solid (24 mg). Compound I-21: HPLC Method B, Rt=3.24 minutes; LCMS 339.1 (M+1); $^1$H NMR consistent with structure. Compound I-22: HPLC Method B, Rt=4.51 minutes; LCMS 367.2 (M+1); $^1$H NMR consistent with structure.

Example 12

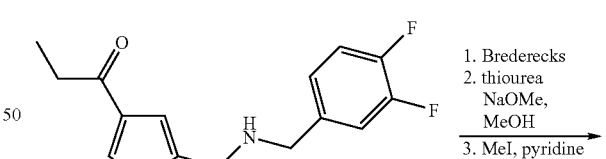
6

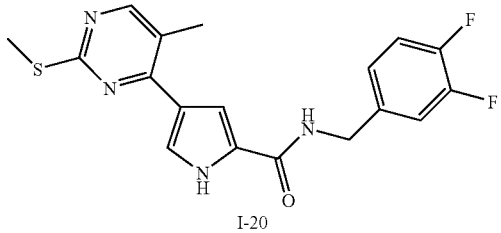
I-20

4-(5-Methyl-2-methylsulfanyl-pyrimidin-4-yl)-1H-pyrrole-2-carboxylic acid 3,4-difluoro-benzylamide (I-20): 6

(1.97 mmol, 575 mg) was dissolved in dry THF (5 mL). Tert-Butoxybis-(dimethylamino)methane (5 mL, 12 eq.) was added and the mixture was stirred at room temperature for 48 hours. Volatiles were then removed in vacuo and the remainder was dried under vacuum to give a brown foam. The intermediate was combined with thiourea (450 mg, 3 eq.) and sodium methoxide (25 wt % in MeOH, 1 mL) in methanol and heated to reflux for 48 hours. The reaction mixture was then diluted with ethyl acetate, washed with brine, dried (MgSO$_4$), filtered and concentrated in vacuo. Alkylation was achieved by treating the unpurified material with methyl iodide (0.37 mL, 3 eq.) and pyridine (0.5 mL, 3 eq.) in methylene chloride at room temperature for 4 hours. The product was purified by flash chromatography on silica (ethyl acetate:hexane gradient) to give a yellow solid (120 mg). HPLC Method B, Rt=6.24 minutes; LCMS 375.1 (M+1), 373.1 (M−1).

Example 13

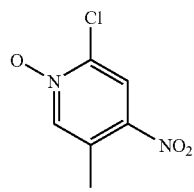

10

2-Chloro-5-methyl-4-nitropyridine N-oxide (10): Following the method of Z. Talik, A. Puszko, *Roczniki Chemii Ann. Soc. Chim. Polonorum,* 1976, 50, 2209, to a suspension of 2-chloro-5-methylpyridine (10 g, 0.078 mol) in acetic anhydride (25 mL), hydrogen peroxide 30% (25 mL) was added in small portions. This mixture was stirred at room temperature for 24 hours and then heated at 60° C. for 30 hours. After removing the excess of acetic acid under reduced pressure, the residue was added in small portions to concentrated sulfuric acid (15 mL). The resulting solution was added to a mixture of concentrated sulfuric acid (15 mL) and fuming nitric acid (25 mL), and then heated at 100° C. for 90 minutes. The reaction mixture was poured on ice, neutralized with solid ammonium carbonate and finally with aqueous ammonia until basic. A precipitate was then formed. After filtration, 10 was isolated as a pale yellow solid (9.4 g, 0.050 mol, HPLC R$_t$=3.272 minutes, FIA ES+ 188.9, ES− 188.0).

Example 14

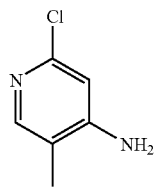

11

4-Amino-2-chloro-5-methylpyridine (11): Iron (1.0 g) was added to a solution of 10 (500 mg, 2.6 mmol) in glacial acetic acid (10 mL). The reaction mixture was then heated at 100° C. for 20 minutes. The suspension was poured on aqueous NaOH 1M and extracted with ethyl acetate. After drying over Na$_2$SO$_4$, the solvent was then evaporated and 11 was isolated as a colorless solid (370 mg, 2.6 mmol, HPLC R$_t$=1.3 min, FIA ES+ 143.0).

Example 15

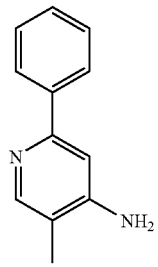

12

4-Amino-5-methyl-2-phenylpyridine (12): Phenylboronic acid (188 mg, 1.5 mmol, 1.1 equiv.) and 11 (200 mg, 1.4 mmol, 1.0 equiv.) were dissolved in benzene (5 mL). Aqueous Na$_2$CO$_3$ (1 mL) was then added, followed by Pd(PPh$_3$)$_4$ (324 mg, 0.28 mmol, 0.2 equiv.). The resulting mixture was refluxed for 16 hours. The reaction mixture was dissolved in ethyl acetate and washed with water. The organic extract was dried over Na$_2$SO$_4$ and the solvent evaporated. The crude material was purified by reverse phase HPLC (Acetonitrile/water/TFA), to give 12 as a colorless solid (160 mg, 0.87 mmol, HPLC R$_t$=3.373 minutes; FIA ES+ 185.1, ES− not observed).

Example 16

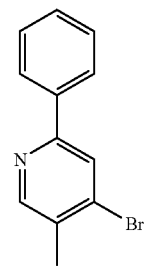

13

4-Bromo-5-methyl-2-phenylpyridine (13): CuBr$_2$ (600 mg, 2.7 mmol, 3.0 equiv.) and tert-butylnitrite (0.5 mL) were mixed in acetonitrile (4 mL). The resulting mixture was heated at 65° C. for 20 minutes. 12 (160 mg, 0.87 mmol, 1.0 equiv.) was then added and the resulting mixture was stirred for 2 hours at 65° C. The reaction mixture was poured on water and extracted with ethyl acetate. The organic layer was washed with NH$_4$OH until no blue color was observed in the aqueous layer. The organic extract was then washed with water, dried over Na$_2$SO$_4$, and the solvent was removed under reduced pressure. The crude residue 13 was purified by preparative TLC on SiO$_2$ (dichloromethane/methanol 95:5). (29 mg, 0.12 mmol, HPLC R$_t$=5.836 minutes, FIA ES+ 247.9, 249.8, ES− not observed). 12 (31 mg, 0.17 mmol) was also recovered.

Example 17

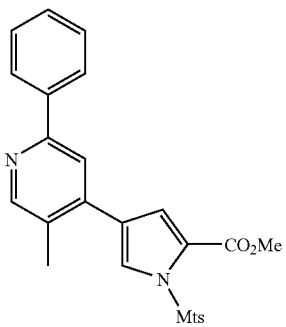

4-(5-Methyl-2-phenylpyridin-4-yl)-1-(2,4,6-trimethyl-benzensulfonyl)-1H-pyrrole-2-carboxylic acid methyl ester (14): 13 (29 mg, 0.12 mmol, 1.0 equiv.) and 4-(4,4,5,5-tetramethyl-[1,3,2]dioxaborolan-2-yl)-1-(2,4,6-trimethyl-benzensulfonyl)-1H-pyrrole-2-carboxylic acid methyl ester (52 mg, 0.12 mmol, 1.0 equiv.) were dissolved in benzene (1.2 mL). After adding aqueous $Na_2CO_3$ (0.2 mL), $Pd(PPh_3)_4$ (28 mg, 0.024 mol, 0.2 equiv.) was then added and the resulting mixture was refluxed for 16 hours. The reaction mixture was dissolved in ethyl acetate and washed with water. After drying the organic layer over $Na_2SO_4$, the solvent was removed under reduced pressure. The crude product 14 was used without further purification (100 mg, HPLC $R_t$=7.005 minutes, ES+ 475.4, ES− not observed).

Example 18

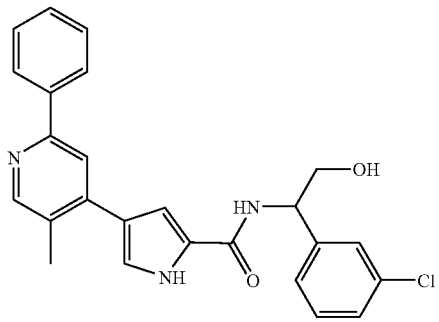

4-(5-Methyl-2-phenylpyridin-4-yl)-1H-pyrrole-2-carboxylic acid[1-(S_-(3-chlorophenylglycinol]amide (I-68): 14 (100 mg, crude) was dissolved in methanol (1.0 mL) and aqueous NaOH 1M (1.0 mL). The mixture was heated at 90° C. for 4 h. After neutralizing with 1M HCl (1.1 mL), the mixture was extracted with ethyl acetate, the organic layer was washed with water and then dried over $Na_2SO_4$. After evaporating the solvent under reduced pressure, the crude residue was dissolved in DMF (1.5 mL). To this solution, EDCI (46 mg, 0.24 mmol, 2.0 equiv.), HOBt (32 mg, 0.24 mmol, 2.0 equiv) and DIEA (0.06 mL, 0.36 mmol, 3.0 equiv.) were added. The reaction mixture was stirred for 30 minutes at room temperature. (S)-3-Chlorophenylglycinol HCl salt (75 mg, 0.36 mmol, 3.0 equiv.) was added and the reaction mixture was then stirred for 16 hours at room temperature. The crude reaction mixture was then dissolved in ethyl acetate. After washing with water, the organic extract was dried over $Na_2SO_4$ and the solvent was removed under reduced pressure. The crude residue was purified by preparative TLC on $SiO_2$ (DCM/methanol 95:5), followed by reverse phase HPLC (Acetonitrile/water/TFA). I-68 was isolated as a colorless solid (3.2 mg, 0.007 mmol, HPLC $R_t$=5.067 minutes; FIA ES+ 432.0, ES− 430.3; LC/MS $R_t$=2.4 min, ES+ 432.0, ES− 430.2; 1HNMR (CD3OD) d 2.7 (s, 3H), 3.85 (m, 2H), 5.15 (t, 1H), 7.3 (m, 4H), 7.4 (s, 1H), 7.7 (m, 4H), 7.9 (m, 2H), 8.3 (s, 1H), 8.5 (s, 1H).

Biological Testing

The activity of the present compounds as protein kinase inhibitors may be assayed in vitro, in vivo or in a cell line. In vitro assays include assays that determine inhibition of either the phosphorylation activity or ATPase activity of the activated protein kinase. Alternate in vitro assays quantitate the ability of the inhibitor to bind to the protein kinase. Inhibitor binding may be measured by radiolabelling the inhibitor prior to binding, isolating the inhibitor/protein kinase complex and determining the amount of radiolabel bound. Alternatively, inhibitor binding may be determined by running a competition experiment where new inhibitors are incubated with the protein kinase bound to known radioligands. The details of the conditions used for performing these assays are set forth in Examples 19 through 26.

Example 19

ERK2 Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $K_i$ and $IC_{50}$ were evaluated from the rate data as a function of inhibitor concentration.

Table 3 shows the results of the activity of selected compounds of this invention in the ERK2 inhibition assay. The compound numbers correspond to the compound numbers in Tables 1 and 2. Compounds having an activity designated as "A" provided a $K_i$ of less than 0.1 micromolar or an $IC_{50}$ of less than 0.1 micromolar; compounds having an activity designated as "B" provided a $K_i$ of between 0.1 and 1.0 micromolar or an $IC_{50}$ of between 0.1 and 0.1 micromolar; and compounds having an activity designated as "C" provided a $K_i$ of greater than 1.0 micromolar or an $IC_{50}$ of greater than 1.0 micromolar.

TABLE 4

ERK2 Inhibitory Activity of Selected Compounds

| No. I- | $K_i$ | $IC_{50}$ |
|---|---|---|
| 1 | A | — |
| 2 | B | — |
| 3 | B | — |
| 4 | C | — |

TABLE 4-continued

ERK2 Inhibitory Activity of Selected Compounds

| No. I- | $K_i$ | $IC_{50}$ |
|---|---|---|
| 5 | C | — |
| 6 | C | — |
| 7 | C | — |
| 8 | C | — |
| 22 | A | — |
| 24 | A | — |
| 25 | A | — |
| 46 | — | C |
| 47 | — | A |
| 48 | — | A |
| 49 | — | B |
| 50 | — | C |
| 51 | — | C |
| 52 | — | A |
| 53 | — | A |
| 54 | — | A |
| 55 | — | B |
| 56 | — | B |
| 57 | — | A |
| 58 | — | A |
| 59 | — | A |

Example 20

ERK2 Inhibition: Cell Proliferation Assay

Compounds may be assayed for the inhibition of ERK2 by a cell proliferation assay. In this assay, a complete media is prepared by adding 10% fetal bovine serum and penicillin/streptomycin solution to RPMI 1640 medium (JRH Biosciences). Colon cancer cells (HT-29 cell line) are added to each of 84 wells of a 96 well plate at a seeding density of 10,000 cells/well/150 µL. The cells are allowed to attach to the plate by incubating at 37° C. for 2 hours. A solution of test compound is prepared in complete media by serial dilution to obtain the following concentrations: 20 µM, 6.7 µM, 2.2 µM, 0.74 µM, 0.25 µM, and 0.08 µM. The test compound solution (50 µL) is added to each of 72 cell-containing wells. To the 12 remaining cell-containing wells, only complete media (200 µL) is added to form a control group in order to measure maximal proliferation. To the remaining 12 empty wells, complete media is added to form a vehicle control group in order to measure background. The plates are incubated at 37° C. for 3 days. A stock solution of $^3$H-thymidine (1 mCi/mL, New England Nuclear, Boston, Mass.) is diluted to 20 µCi/mL in RPMI medium then 20 µL of this solution is added to each well. The plates are further incubated at 37° C. for 8 hours then harvested and analyzed for $^3$H-thymidine uptake using a liquid scintillation counter.

Example 21

ERK1 Inhibition Assay

Compounds may be assayed for the inhibition of ERK1 by a spectrophotometric coupled-enzyme assay (Fox et al (1998) *Protein Sci* 7, 2249). In this assay, a fixed concentration of activated ERK1 (20 nM) is incubated with various concentrations of the compound in DMSO (2.0%) for 10 min. at 30° C. in 0.1 M HEPES buffer, pH 7.6, containing 10 mM MgCl$_2$, 2.5 mM phosphoenolpyruvate, 200 µM NADH, 30 µg/mL pyruvate kinase, 10 µg/mL lactate dehydrogenase, and 150 µM erktide peptide. The reaction is initiated by the addition of 140 µM ATP (20 µL). The rate of decrease of absorbance at 340 nM is monitored. The $K_i$ is evaluated from the rate data as a function of inhibitor concentration.

Example 22

GSK-3 Inhibition Assay

Compounds are screened for their ability to inhibit GSK-3β (AA 1-420) activity using a standard coupled enzyme system (Fox et al. (1998) *Protein Sci.* 7, 2249). Reactions are carried out in a solution containing 100 mM HEPES (pH 7.5), 10 mM MgCl$_2$, 25 mM NaCl, 300 µM NADH, 1 mM DTT and 1.5% DMSO. Final substrate concentrations in the assay are 20 µM ATP (Sigma Chemicals, St Louis, Mo.) and 300 µM peptide (HSSPHQS(PO$_3$H$_2$)EDEEE, American Peptide, Sunnyvale, Calif.). Reactions are carried out at 30° C. and 20 nM GSK-3β. Final concentrations of the components of the coupled enzyme system are 2.5 mM phosphoenolpyruvate, 300 µM NADH, 30 µg/ml pyruvate kinase and 10 µg/ml lactate dehydrogenase.

An assay stock buffer solution is prepared containing all of the reagents listed above with the exception of ATP and the test compound of interest. The assay stock buffer solution (175 µl) is incubated in a 96 well plate with 5 µl of the test compound of interest at final concentrations spanning 0.002 µM to 30 µM at 30° C. for 10 min. Typically, a 12 point titration is conducted by preparing serial dilutions (from 10 mM compound stocks) with DMSO of the test compounds in daughter plates. The reaction is initiated by the addition of 20 µl of ATP (final concentration 20 µM). Rates of reaction are obtained using a Molecular Devices Spectramax plate reader (Sunnyvale, Calif.) over 10 min at 30° C. The $K_i$ values are determined from the rate data as a function of inhibitor concentration.

Example 23

AURORA-2 Inhibition Assay

Compounds may be screened in the following manner for their ability to inhibit Aurora-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 µM NADH, 30 mg/ml pyruvate kinase, 10 mg/ml lactate dehydrogenase, 40 mM ATP, and 800 µM peptide (LRRASLG, American Peptide, Sunnyvale, Calif.) is added a DMSO solution of a compound of the present invention to a final concentration of 30 µM. The resulting mixture is incubated at 30° C. for 10 minutes. The reaction is initiated by the addition of 10 µL of Aurora-2 stock solution to give a final concentration of 70 nM in the assay. The rates of reaction are obtained by monitoring absorbance at 340 nm over a 5 minute read time at 30° C. using a BioRad Ultramark plate reader (Hercules, Calif.). The $K_i$ values are determined from the rate data as a function of inhibitor concentration.

Example 24

CDK-2 Inhibition Assay

Compounds may be screened in the following manner for their ability to inhibit CDK-2 using a standard coupled enzyme assay (Fox et al (1998) *Protein Sci* 7, 2249).

To an assay stock buffer solution containing 0.1M HEPES 7.5, 10 mM MgCl$_2$, 1 mM DTT, 25 mM NaCl, 2.5 mM phosphoenolpyruvate, 300 mM NADH, 30 mg/ml pyruvate kinase, 10 mg/ml lactate dehydrogenase, 100 mM ATP, and 100 μM peptide (MAHHHRSPRKRAKKK, American Peptide, Sunnyvale, Calif.) is added a DMSO solution of a compound of the present invention to a final concentration of 30 μM. The resulting mixture is incubated at 30° C. for 10 min.

The reaction is initiated by the addition of 10 μL of CDK-2/Cyclin A stock solution to give a final concentration of 25 nM in the assay. The rates of reaction are obtained by monitoring absorbance at 340 nm over a 5-minute read time at 30° C. using a BioRad Ultramark plate reader (Hercules, Calif.). The K$_i$ values are determined from the rate data as a function of inhibitor concentration.

Example 25

AKT3 Inhibition Assay

Compounds may be screened for their ability to inhibit AKT3 using a standard coupled enzyme assay (Fox et al., *Protein Sci.,* (1998) 7, 2249). Assays are carried out in a mixture of 100 mM HEPES 7.5, 10 mM MgCl$_2$, 25 mM NaCl, 1 mM DTT and 1.5% DMSO. Final substrate concentrations in the assay are 170 μM ATP (Sigma Chemicals) and 200 μM peptide (RPRAATF, American Peptide, Sunnyvale, Calif.). Assays are carried out at 30° C. and 45 nM AKT3. Final concentrations of the components of the coupled enzyme system are 2.5 mM phosphoenolpyruvate, 300 μM NADH, 30 μg/ML pyruvate kinase and 10 μg/ml lactate dehydrogenase.

An assay stock buffer solution may be prepared containing all of the reagents listed above, with the exception of AKT3, DTT, and the test compound of interest. 56 μl of the stock solution is placed in a 384 well plate followed by addition of 1 μl of 2 mM DMSO stock containing the test compound (final compound concentration 30 μM). The plate is preincubated for about 10 minutes at 30° C. and the reaction initiated by addition of 10 μl of enzyme (final concentration 45 nM) and 1 mM DTT. Rates of reaction are obtained using a BioRad Ultramark plate reader (Hercules, Calif.) over a 5 minute read time at 30° C. Compounds showing greater than 50% inhibition versus standard wells containing the assay mixture and DMSO without test compound are titrated to determine IC$_{50}$ values.

Example 26

Rock Inhibition Assay

Compounds were screened for their ability to inhibit ROCK using a standard coupled enzyme assay (Fox et al., *Protein Sci.* 1998, 7, 2249). Reactions were carried out in 100 mM HEPES pH 7.5, 10 mM MgCl2, 25 mM NaCl, 1 mM DTT and 1.5% DMSO. Final substrate concentrations in the assay were 13 AM ATP (Sigma chemicals) and 200 μM peptide (KKRNRTLSV, American Peptide, Sunnyvale, Calif.). Assays were carried out at 30° C. and 200 nM ROCK. Final concentrations of the components of the coupled enzyme system were 2.5 mM phosphoenolpyruvate, 400 μM NADH, 30 μg/mL pyruvate kinase and 10 μg/mL lactate dehydrogenase.

An assay stock buffer solution was prepared containing all of the reagents listed above, with the exception of ROCK, DTT, and the test compound of interest. 56 μL of the test reaction was placed in a 384 well plate followed by addition of μL of 2 mM DMSO stock containing the test compound (final compound concentration 30 μM). The plate was pre-incubated for about 10 minutes at 30° C. and the reaction initiated by addition of 10 μL of enzyme (final concentration 100 nM). Rates of reaction were obtained using a BioRad Ultramark plate reader (Hercules, Calif.) over a 5 minute read time at 30° C. Compounds showing >50% inhibition versus standard wells containing DMSO, but no compound, were titrated and IC$_{50}$s determined using a similar protocol.

While we have presented a number of embodiments of this invention, it is apparent that our basic construction can be altered to provide other embodiments which utilize the compounds and methods of this invention. Therefore, it will be appreciated that the scope of this invention is to be defined by the appended claims rather than by the specific embodiments which have been represented by way of example.

We claim:
1. A compound of general formula I:

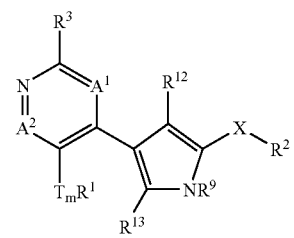

or a pharmaceutically acceptable salt thereof, wherein:
A$_1$ is N;
A$_2$ is CR$^{11}$;
T is selected from —C(R$^7$)$_2$—, —C(O)—, —C(O)C(O)—, —C(O)NR$^7$—, —C(O)NR$^7$NR$^7$—, —CO$_2$—, —OC(O)—, —NR$^7$CO$_2$—, —O—, —NR$^7$C(O)NR$^7$—, —OC(O)NR$^7$—, —NR$^7$NR$^7$—, —NR$^7$C(O)—, —S—, —SO—, —SO$_2$—, —NR$^7$—, —SO$_2$NR$^7$—, —NR$^7$SO$_2$—, or —NR$^7$SO$_2$NR$^7$—;
m is selected from zero or one;
R$^1$ is selected from: (a) hydrogen, CN, halogen, R, N(R$^7$)$_2$, OR, or OH, wherein m is zero; or (b) hydrogen or R, wherein m is one;
X is selected from —C(O)—, —C(O)NR$^7$ —, —NR$^7$C(O)—, —NR$^7$SO$_2$—, —SO$_2$NR$^7$—, —S(O)—, or —SO$_2$—;
R$^2$ is selected from —(CH$_2$)$_y$R$^5$, —(CH$_2$)$_y$CH(R$^5$)$_2$, —(CH$_2$)$_y$CH(R$^8$)(R$^5$), —(CH$_2$)$_y$CH(R$^8$)CH(R$^5$)$_2$, —N(R$^4$)$_2$, —NR$^4$(CH$_2$)$_y$N(R$^4$)$_2$, —ON(R$^7$)$_2$, or —NR$^7$OR$^6$;
y is 0-6;
R$^3$ is selected from —R, —OR$^6$, —S(O)R$^6$, or —ON(R$^7$)$_2$;
R$^6$ is selected from hydrogen or —R;
each R is independently selected from an optionally substituted group selected from C$_{1-6}$ aliphatic; 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four hetero atoms independently selected from nitrogen, sulfur, or oxygen;

each $R^4$ is independently selected from —R, —$R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from —R, —OR, —$CO_2R$, —$(CH_2)_yN(R^7)_2$, —$N(R^7)_2$, —$OR^7$, —$SR^7$, —$NR^7C(O)R^7$, —$NR^7CON(R^7)_2$, —$C(O)N(R^7)_2$, —$SO_2R^7$, —$NR^7SO_2R^7$, —$C(O)R^7$, —CN, or —$SO_2N(R^7)_2$;

each $R^7$ is independently selected from hydrogen or an optionally substituted $C_{1-6}$ aliphatic group, or two $R^7$ groups bound to the same nitrogen are taken together with the nitrogen to form a 3-7 membered heterocyclic ring having 0-2 heteroatoms in addition to the nitrogen, independently selected from nitrogen, oxygen, or sulfur;

$R^8$ is selected from —R, —$(CH_2)_wOR^7$, —$(CH_2)_wN(R^4)_2$, or —$(CH_2)_wSR^7$;

each w is independently selected from 0-4;

$R^9$ is selected from hydrogen, an optionally substituted $C_{1-6}$ aliphatic group, $C(O)R^7$, $C(O)OR^7$, or $SO_2R^7$;

$R^{11}$ is selected from $R^7$, halogen, CN, $NO_2$, $OR^7$, $SR^7$, $N(R^7)_2$, $C(O)R^7$, or $CO_2R^7$; and each of $R^{12}$ and $R^{13}$ is hydrogen.

2. The compound according to claim 1 wherein said compound has one or more features selected from the group consisting of:
(a) X is selected from —C(O)— or —C(O)$NR^7$;
(b) $R^3$ is —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;
(c) $T_mR^1$ is hydrogen, amino, OH, 3-6 membered carbocyclyl, or an optionally substituted group selected from $C_{1-6}$ aliphatic or a 5-6 membered aryl or heteroaryl ring;
(d) $R^2$ is —$NR^4(CH_2)_yN(R^4)_2$, —$(CH_2)_yR^5$, —$(CH_2)_yCH(R^5)_2$, —$(CH_2)_yCH(R^8)(R^5)$, or —$(CH_2)_yCH(R^8)CH(R^5)_2$;
(e) $R^4$ is R, $R^7$, or —$(CH_2)_yCH(R^5)_2$; and
(f) $R^5$ is an optionally substituted group selected from $C_{1-6}$ aliphatic, phenyl, naphthyl, 5-6 membered heteroaryl, or 5-6 membered heterocyclyl.

3. The compound according to claim 2 wherein said compound has one or more features selected front the group consisting of:
(a) X is selected from —C(O)— or —C(O)$NR^7$;
(b) $R^3$ is selected from optionally substituted phenyl, methyl, ethyl, propyl, cyclopropyl, pyridinyl, morpholinyl, piperidinyl, piperazinyl, OH, O-methyl, O-ethyl, or —$CH_2$— morpholin-4-yl;
(c) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$;
(d) $R^2$ is —$(CH_2)_yR^5$, —$(CH_2)_yCH(R^5)_2$, —$(CH_2)_yCH(R^8)(R^5)$, or —$(CH_2)_yCH(R^8)CH(R^5)_2$, wherein $R^8$ is OH, $NH_2$, $CH_2OH$, $CH_2NH_2$, or $CH_2CH_2NH_2$; and
(e) $R^5$ is —$CH_2OH$, —$(CH_2)_2OH$, isopropyl, or an optionally substituted group selected from pyrrolidinyl, morpholinyl, piperidinyl, piperazinyl, methyldiazepanyl, phenylpiperazineyl, pyridinyl, imidazolyl, furanyl, tetrahydroisoquinoline, tetrahydrofuranyl, cyclohexyl, phenyl, or benzyl.

4. The compound according to claim 1 wherein said compound is of formula I':

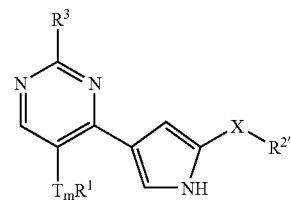

or a pharmaceutically acceptable salt or derivative thereof, wherein:
$R^{2'}$ is selected from —$(CH_2)_yCH(R^5)_2$, —$(CH_2)_yCH(R^8)(R^5)$, or —$(CH_2)_yCH(R^8)CH(R^5)_2$.

5. The compound according to claim 4 wherein said compound has one or more features selected from the group consisting of:
(a) X is selected from —C(O)— or —C(O)$NR^7$;
(b) $R^3$ is —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;
(c) $T_mR^1$ is hydrogen, amino, OH, 3-6 m,membered carbocyclyl, or an optionally substituted group selected from $C_{1-6}$ aliphatic or a 5-6 membered aryl or heteroaryl ring; and
(d) $R^5$ is R, $OR^7$, or $N(R^7)_2$, wherein R is carbocyclic, or an optionally substituted 5 or 6-membered aryl or heteroaryl ring.

6. The compound according to claim 5 wherein said compound has one or more features selected from the group consisting of:
(a) X is selected from —C(O)— or —C(O)$NR^7$;
(b) $R^3$ is selected from optionally substituted phenyl, methyl, ethyl, propyl, cyclopropyl, pyridinyl, morpholinyl, piperidinyl, piperazinyl, OH, O-methyl, O-ethyl, or —$CH_2$— morpholin-4-yl;
(c) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and
(d) $R^5$ is OH, $NH_2$, carbocyclic, or an optionally substituted phenyl or pyridyl ring.

7. The compound according to claim 1 wherein said compound is of formula I":

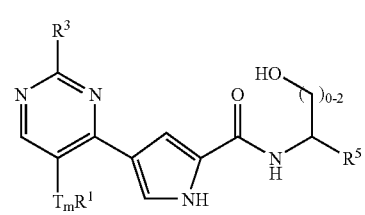

or a pharmaceutically acceptable salt thereof.

8. The compound according to claim 7 wherein said compound has one or more features selected from the group consisting of:
(a) $R^3$ is —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;

(b) $T_mR^1$ is hydrogen, $N(R^7)_2$, OH, 3-6 membered carbocyclyl, or an optionally substituted group selected from $C_{1-6}$ aliphatic or a 5-6 membered aryl or heteroaryl ring; and (c) $R^5$ is an optionally substituted 6-membered aryl, heteroaryl, or carbocyclic ring.

9. The compound according to claim 8 wherein said compound has one or more features selected from the group consisting of:
(a) $R^3$ is selected from optionally substituted phenyl, methyl, ethyl, propyl, cyclopropyl, pyridinyl, morpholinyl, piperidinyl, piperazinyl, OH, O-methyl, O-ethyl, or —$CH_2$— morpholin-4-yl;
(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and
(c) $R^5$ is cyclohexyl or an optionally substituted phenyl or pyridyl ring.

10. The compound according to claim 1 wherein said compound is of formula I°:

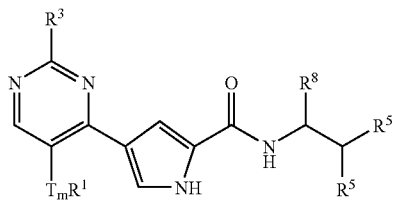

or a pharmaceutically salt thereof, wherein:

T is selected from —$C(R^7)_2$—, —C(O)—, —C(O)C(O)—, —C(O)$NR^7$—, —C(O)$NR^7NR^7$—, —$CO_2$—, —OC(O)—, —$NR^7CO_2$—, —O—, —$NR^7C(O)NR^7$—, —OC(O)$NR^7$—, —$NR^7NR^7$—, —$NR^7C(O)$—, —S—, —SO—, —$SO_2$—, —$NR^7$—, —$SO_2NR^7$—, —$NR^7SO_2$—, or —$NR^7SO_2NR^7$—;

m is selected from zero or one;

$R^1$ is selected from: (a) hydrogen, CN, halogen, R, $N(R^7)_2$, OR, or OH, wherein m is zero; or (b) hydrogen or R, wherein m is one;

$R^3$ is selected from —R, —$OR^6$, —$S(O)R^6$, or —$ON(R^7)_2$;

$R^6$ is selected from hydrogen or —R;

each R is independently selected from an optionally substituted group selected from $C_{1-6}$ aliphatic; 3-7 membered saturated, partially saturated, or aromatic monocyclic ring having zero to three heteroatoms independently selected from nitrogen, sulfur, or oxygen; or an 8-10 membered saturated, partially saturated, or aromatic bicyclic ring having zero to four heteroatoms independently selected from nitrogen, sulfur, or oxygen;

each $R^4$ is independently selected from —R, —$R^7$, —$COR^7$, —$CO_2R$, —$CON(R^7)_2$, —$SO_2R^7$, —$(CH_2)_yR^5$, or —$(CH_2)_yCH(R^5)_2$;

each $R^5$ is independently selected from —R, —OR, —$CO_2R$, —$(CH_2)_yN(R^7)_2$, —$N(R^7)_2$, —$OR^7$, —$SR^7$, —$NR^7C(O)R^7$, —$NR^7CON(R^7)_2$, —$C(O)N(R^7)_2$, —$SO_2R^7$, —$NR^7SO_2R^7$, —$C(O)R^7$, —CN, or —$SO_2N(R^7)_2$;

each $R^7$ is independently selected from hydrogen or an optionally substituted $C_{1-6}$ aliphatic group, or two $R^7$ groups bound to the same nitrogen are taken together with the nitrogen to form a 3-7 membered heterocyclic ring having 0-2 heteroatoms in addition to the nitrogen, independently selected from nitrogen, oxygen, or sulfur;

$R^8$ is selected from —R, —$(CH_2)_wOR^7$, —$(CH_2)_wN(R^4)_2$, or —$(CH_2)_wSR^7$; and each w is independently selected from 0-4.

11. The compound according to claim 10 wherein said compound has one or more features selected from the group consisting of:
(a) $R^3$ is —OH; —O($C_{1-6}$ aliphatic); 3-6 membered carbocyclyl; or an optionally substituted group selected from $C_{1-6}$ aliphatic or a 5-6 membered aryl, heteroaryl, or heterocyclyl ring;
(b) $T_mR^1$ is hydrogen, amino, OH, 3-6 membered carbocyclyl, or an optionally substituted group selected from $C_{1-6}$ aliphatic or a 5-6 membered aryl or heteroaryl ring; and
(c) $R^5$ is R, $OR^7$, or $N(R^7)_2$, wherein R is carbocyclic, or an optionally substituted 5 or 6-membered aryl or heteroaryl ring.

12. The compound according to claim 11 wherein said compound has one or more features selected from the group consisting of:
(a) $R^3$ is selected from optionally substituted phenyl, methyl, ethyl, propyl, cyclopropyl, pyridinyl, morpholinyl, piperidinyl, piperazinyl, OH, O-methyl, O-ethyl, or —$CH_2$— morpholin-4-yl;
(b) $T_mR^1$ is selected from optionally substituted phenyl, methyl, ethyl, propyl, cyclopropyl, cyclohexyl, $CH_2OCH_3$, $CH_2OH$, OH, $NH_2$, $NHCH_3$, NHAc, NHC(O)$NHCH_3$, or $CH_2NHCH_3$; and
(c) $R^5$ is OH, $NH_2$, carbocyclic, or an optionally substituted phenyl or pyridyl ring.

13. The compound according to claim 1 of the formula I:

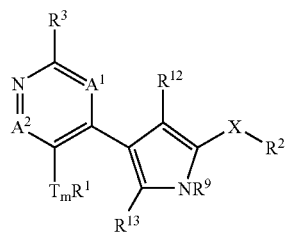

wherein X is —C(O)—, $A_1$ is N, $A_2$ is CH, $R^9$ is hydrogen, and $R^{12}$ and $R^{13}$ is hydrogen, selected from any of the following compounds:

| No. I- | R³ | TmR¹ | R² |
|---|---|---|---|
| 1 | 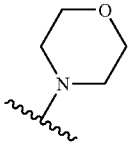 | Methyl | 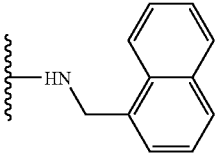 |
| 2 | 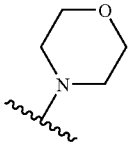 | Methyl | 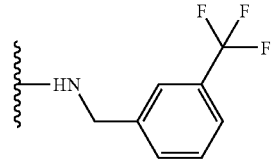 |
| 3 | 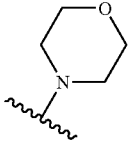 | Methyl | 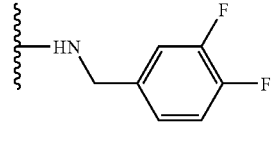 |
| 4 | 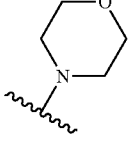 | 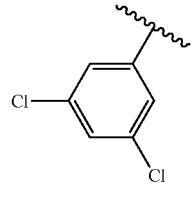 | 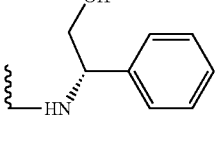 |
| 5 | 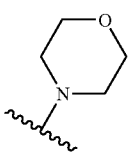 | 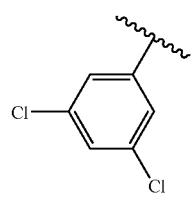 | 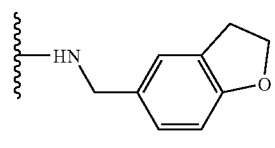 |
| 6 | 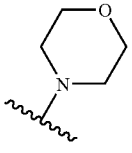 | 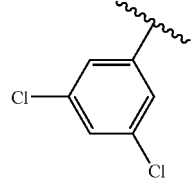 | 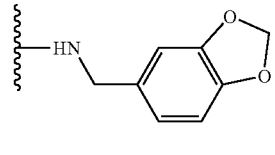 |
| 7 | 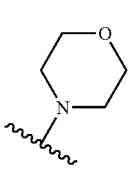 | Methyl | 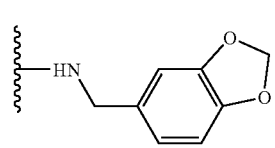 |
| 8 | 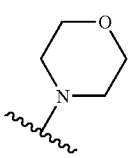 | 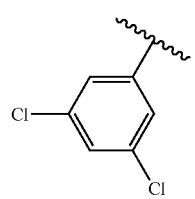 | 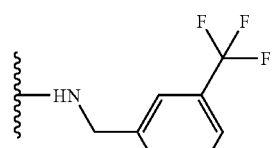 |

| No. I- | R³ | TₘR¹ | R² |
|---|---|---|---|
| 9 | morpholine (N-linked) | 3,5-dichlorophenyl | -HN-CH(Ph)-CH₂OH (S) |
| 10 | morpholine (N-linked) | 3,5-dichlorophenyl | -HN-CH₂-(3,4-difluorophenyl) |
| 11 | morpholine (N-linked) | 3,5-dichlorophenyl | -HN-CH₂-(4-methylsulfonylphenyl) |
| 12 | morpholine (N-linked) | 3-fluoro-5-(trifluoromethyl)phenyl | -HN-CH₂-(3,4-difluorophenyl) |
| 13 | morpholine (N-linked) | 3-fluoro-5-(trifluoromethyl)phenyl | -HN-CH₂-(2,3-dihydrobenzofuran-5-yl) |
| 14 | morpholine (N-linked) | 3-fluoro-5-(trifluoromethyl)phenyl | -HN-CH₂-(benzo[1,3]dioxol-5-yl) |
| 15 | morpholine (N-linked) | 3-fluoro-5-(trifluoromethyl)phenyl | -HN-CH₂-(3-(trifluoromethyl)phenyl) |

| No. I- | R³ | TₘR¹ | R² |
|---|---|---|---|
| 16 | morpholine (N-linked) | 3-fluoro-5-(trifluoromethyl)phenyl | -HN-CH₂-(4-methylsulfonylphenyl) |
| 17 | morpholine (N-linked) | 3-fluoro-5-(trifluoromethyl)phenyl | -HN-CH(Ph)-CH₂OH |
| 18 | morpholine (N-linked) | Methyl | -HN-CH₂-phenyl |
| 19 | morpholine (N-linked) | Methyl | -HN-CH₂-(2,4-dichlorophenyl) |
| 21 | HO- | Methyl | -HN-CH(Ph)-CH₂OH |
| 22 | ethoxy | Methyl | -HN-CH(Ph)-CH₂OH |
| 23 | cyclopropyl | Methyl | -HN-CH(Ph)-CH₂OH |
| 24 | phenyl | Methyl | -HN-CH(Ph)-CH₂OH |

-continued
| No. I- | R³ | TₘR¹ | R² |
|---|---|---|---|
| 25 | methyl | methyl | 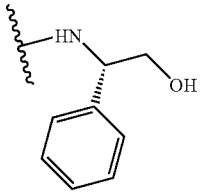 |
| 26 | 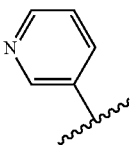 | Methyl | 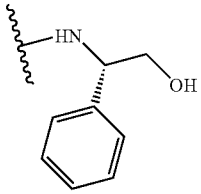 |
| 27 | 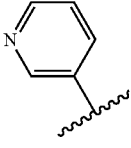 | —CH₂OH | 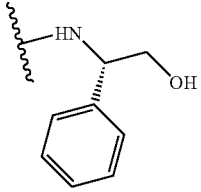 |
| 28 |  | Methyl | 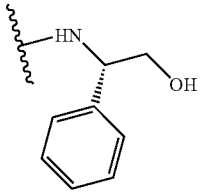 |
| 29 | 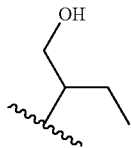 | —CH₂OH | 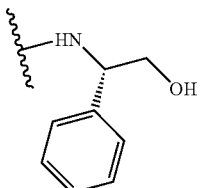 |
| 30 | 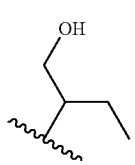 | —CH₂OH | 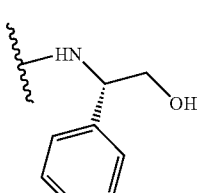 |
| 31 | 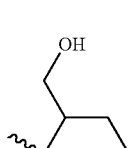 | —CH₂NH₂ | 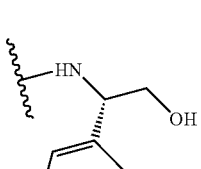 |

| No. I- | R³ | TₘR¹ | R² |
|---|---|---|---|
| 32 | 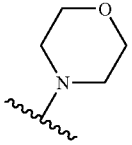 | Methyl | 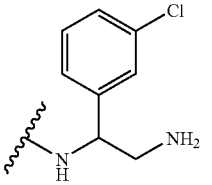 |
| 33 | 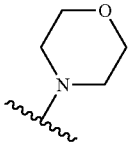 | methyl | 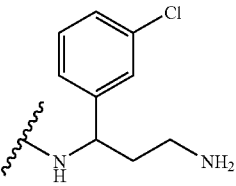 |
| 34 | 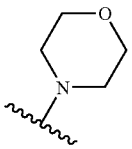 | H | 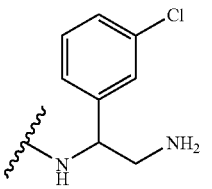 |
| 35 | 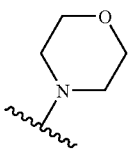 | H | 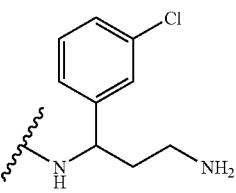 |
| 36 | 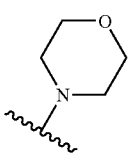 | 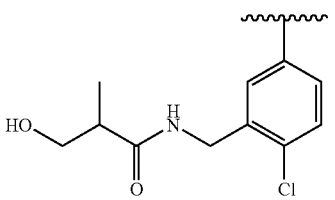 | 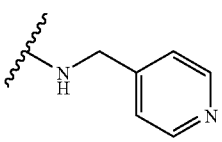 |
| 37 | 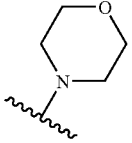 | 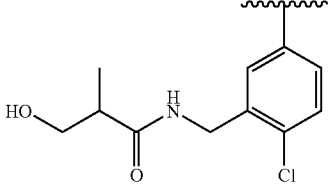 | 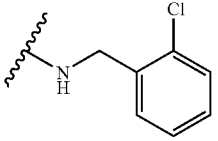 |
| 38 | 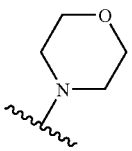 | 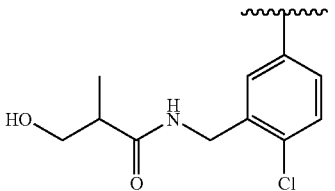 | 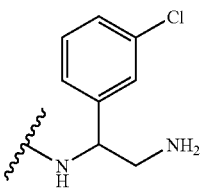 |

| No. I- | R³ | TₘR¹ | R² |
|---|---|---|---|
| 39 | 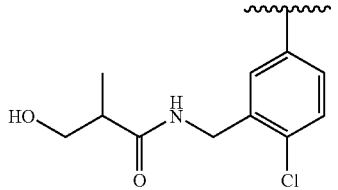 | 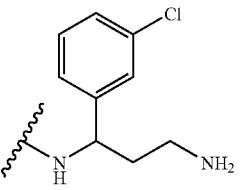 | 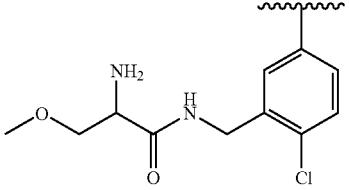 |
| 40 | 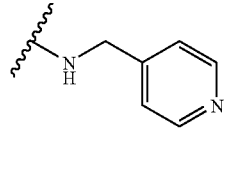 | 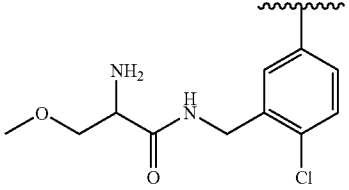 | 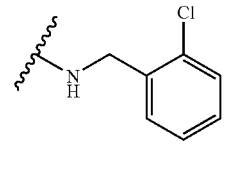 |
| 41 | 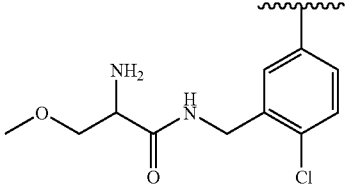 | 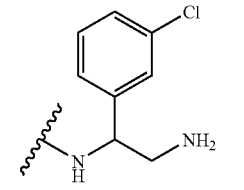 | 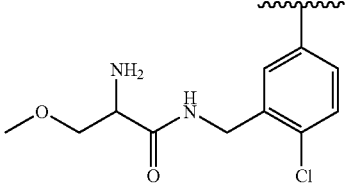 |
| 42 | 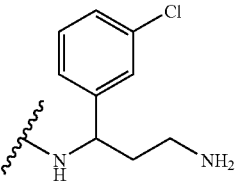 | 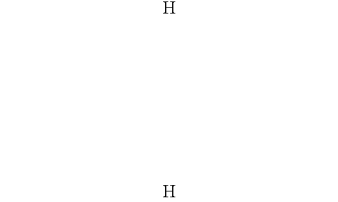 | 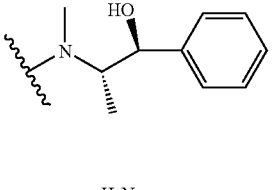 |
| 43 |  | | |
| 44 | | H | |
| 45 | 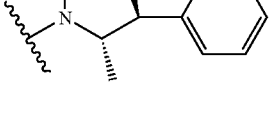 | H | |

14. The compound according to claim 1 of the formula I:

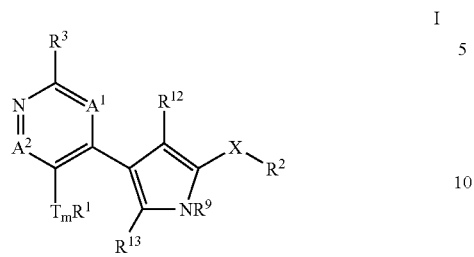

wherein X is —C(O)—, and R¹³ is hydrogen, selected from any one of the following compounds:

| No. I- | A¹ | R³ | TₘR¹ | R⁹ | R¹² | R² |
|---|---|---|---|---|---|---|
| 47 | N | cyclopropyl | Methyl | H | H | NH-CH(CH₂OH)-phenyl |
| 48 | N | phenyl | Methyl | H | H | NH-CH(CH₂OH)-phenyl |
| 49 | N | Methyl | Methyl | H | H | NH-CH(CH₂OH)-phenyl |
| 50 | N | —OH | Methyl | H | H | NH-CH(CH₂OH)-phenyl |
| 53 | N | 3-pyridyl | Methyl | H | H | NH-CH(CH₂OH)-phenyl |
| 55 | N | pyrazinyl | Methyl | H | H | NH-CH(CH₂OH)-phenyl |

-continued

| No. I- | A¹ | R³ | T_mR¹ | R⁹ | R¹² | R² |
|---|---|---|---|---|---|---|
| 58 | N | 4-(C(O)NH₂)-phenyl | Methyl | H | H | NH-CH(CH₂OH)-phenyl |
| 59 | N | 4-(CH₃)-phenyl | Methyl | H | H | NH-CH(CH₂OH)-phenyl |

15. A composition comprising a compound according to claim 1, and a pharmaceutically acceptable carrier, adjuvant, or vehicle.

16. The composition according to claim 15, additionally comprising an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders.

17. A method of treating or lessening the severity of a proliferative disorder, wherein said proliferative disorder is breast cancer, colon cancer, kidney carcinoma, lung cancer, melanoma, ovarian cancer, pancreatic cancer, or prostate cancer; diabetes; a cardiovascular disease, wherein said cardiovascular disease is stroke, atherosclerosis, cardiomegaly, restenosis, or myocardial infraction; allergic disorders; asthma; or a neurological disorder, wherein said neurological disorder is Alzheimer's disease, amyotrophic lateral sclerosis, or cerebral ischemia, comprising the step of administering to said patient a composition according to claim 15.

18. The method according to claim 17, wherein said method is used to treat or lessen the severity of breast cancer, colon cancer, kidney carcinoma, lung cancer, melanoma, ovarian cancer, pancreatic cancer, or prostate cancer.

19. The method according to claim 17, wherein said method is used to treat or lessen the severity of a cardiovascular disease selected from stroke, restenosis, cardiomegaly, arteriosclerosis, or congestive heart failure.

20. The method according to claim 17, wherein said method is used to treat or lessen the severity of a neurological disorder selected from Alzheimer's disease, Parkinson's disease, amyotrophic lateral sclerosis, Huntington's disease, or cerebral ischemia.

21. The method according to claim 17, comprising the additional step of administering to said patient an additional therapeutic agent selected from an anti-proliferative agent, an anti-inflammatory agent, an immunomodulatory agent, a neurotrophic factor, an agent for treating cardiovascular disease, an agent for treating liver disease, an anti-viral agent, an agent for treating blood disorders, an agent for treating diabetes, or an agent for treating immunodeficiency disorders, wherein:

said additional therapeutic agent is appropriate date for the disease being treated; and said additional therapeutic agent is administered together with said composition as a single dosage form or separately from said composition as pan of a multiple dosage form.

22. A composition for coating an implantable device comprising a compound according to claim 1 and a carrier suitable for coating said implantable device.

* * * * *